(12) United States Patent
Apte

(10) Patent No.: US 9,254,285 B2
(45) Date of Patent: Feb. 9, 2016

(54) INHIBITION OF CHOROIDAL NEOVASCULARIZATION

(71) Applicant: Washington University, Saint Louis, MO (US)

(72) Inventor: Rajendra S. Apte, Clayton, MO (US)

(73) Assignee: Washington University, Saint Louis, MO (US)

( * ) Notice: Subject to any disclaimer, the term of this patent is extended or adjusted under 35 U.S.C. 154(b) by 0 days.

(21) Appl. No.: 14/811,011

(22) Filed: Jul. 28, 2015

(65) Prior Publication Data

US 2015/0335633 A1      Nov. 26, 2015

Related U.S. Application Data

(62) Division of application No. 13/918,453, filed on Jun. 14, 2013, now Pat. No. 9,121,019, which is a division of application No. 13/480,024, filed on May 24, 2012, now abandoned.

(60) Provisional application No. 61/489,656, filed on May 24, 2011.

(51) Int. Cl.

| | |
|---|---|
| *A61K 31/47* | (2006.01) |
| *A61K 31/265* | (2006.01) |
| *A61K 9/00* | (2006.01) |
| *A61K 31/421* | (2006.01) |
| *A61K 31/18* | (2006.01) |
| *A61K 31/195* | (2006.01) |
| *A61K 31/4706* | (2006.01) |
| *A61K 31/575* | (2006.01) |
| *A61K 31/58* | (2006.01) |
| *A61K 38/17* | (2006.01) |
| *C12N 15/113* | (2010.01) |

(52) U.S. Cl.
CPC .............. *A61K 31/47* (2013.01); *A61K 9/0048* (2013.01); *A61K 9/0053* (2013.01); *A61K 31/18* (2013.01); *A61K 31/195* (2013.01); *A61K 31/265* (2013.01); *A61K 31/421* (2013.01); *A61K 31/4706* (2013.01); *A61K 31/575* (2013.01); *A61K 31/58* (2013.01); *A61K 38/1709* (2013.01); *C12N 15/113* (2013.01)

(58) Field of Classification Search
None
See application file for complete search history.

(56) References Cited

PUBLICATIONS

Chen et al. Proc. Nat'l Acad. Sci. USA 107: 7401-7406 (2010).*
Neale et al. Proc. Nat'l Acad. Sci. USA 107: 7395-7400 (2010).*
Tanigawa, H., et al., Expression of Cholesteryl Ester Transfer Protein in Mice Promotes Macrophage Reverse Cholesterol Transport, Circulation, Aug. 20, 2007, 116, 1267-1273.

\* cited by examiner

*Primary Examiner* — Doug Schultz
(74) *Attorney, Agent, or Firm* — Zackson Law LLC; Saul L. Zackson

(57) ABSTRACT

Methods of treatment of diseases that include or are characterized by inappropriate or pathological neovascularization are disclosed. These diseases include diseases of the eye, such as diabetic retinopathy, retinopathy of prematurity, and choroidal neovascularization which can occur in age-related macular degeneration (AMD). Disclosed methods include administering agents that cause directly or indirectly upregulation of the ABCA1 transporter protein in macrophages. These agents include, without limitation, LXR agonists. In some embodiments, inhibitors of CETP expression or activity can also be effective. Administration routes can include, without limitation, intraocular, periocular, or systemic administration.

6 Claims, 14 Drawing Sheets

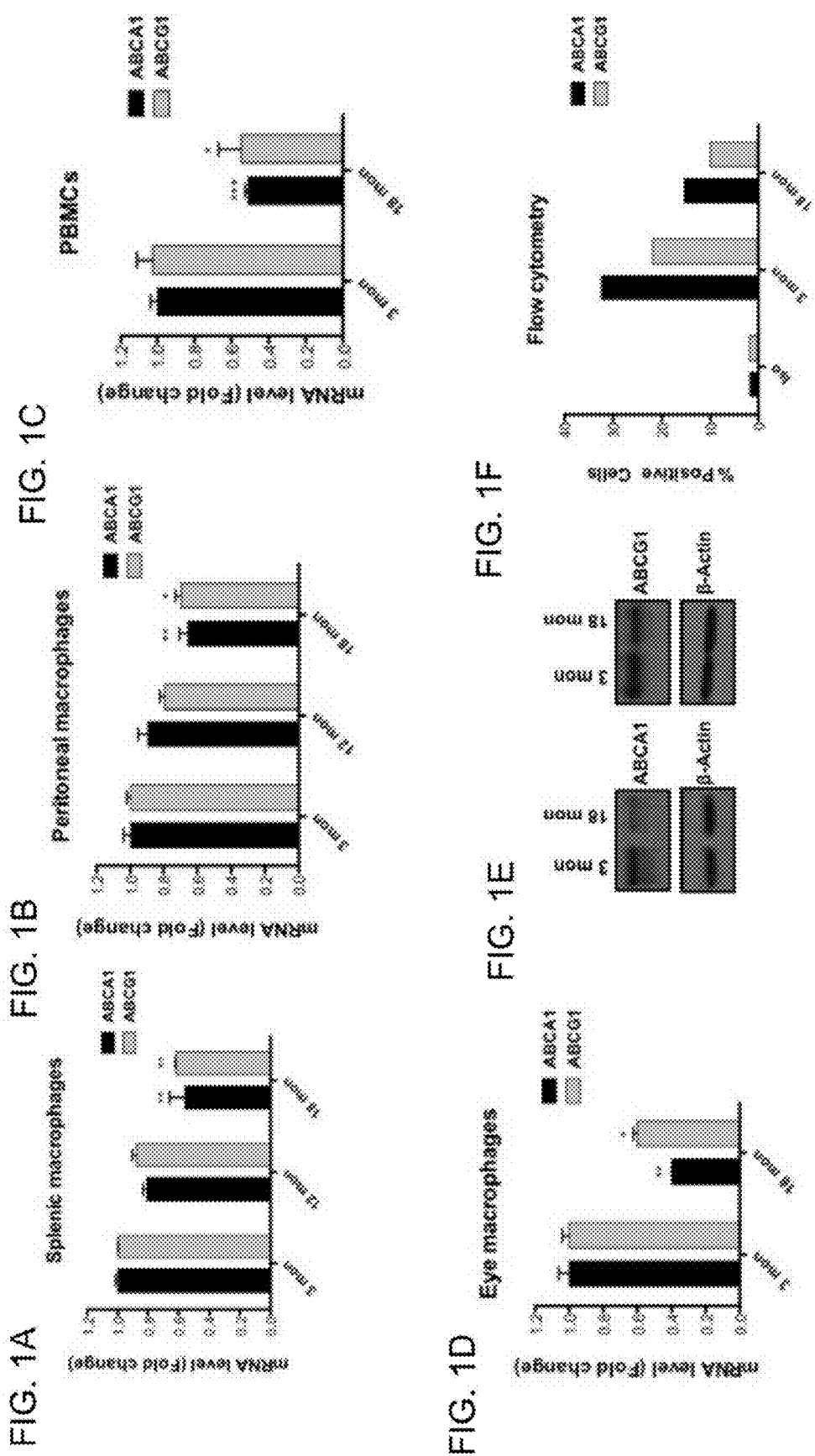

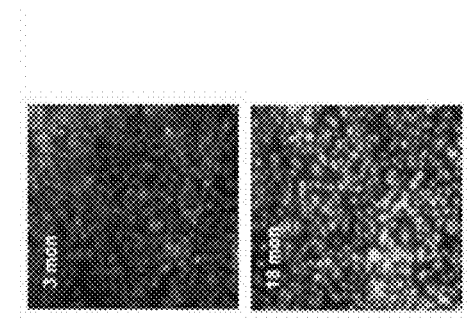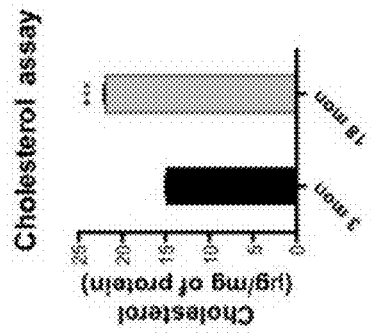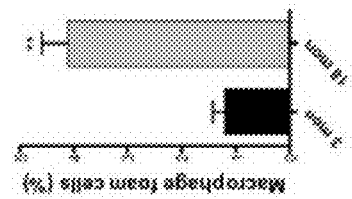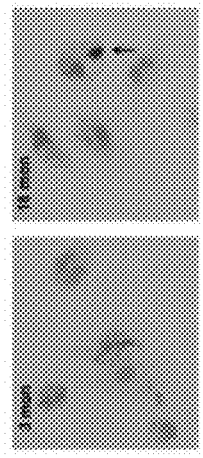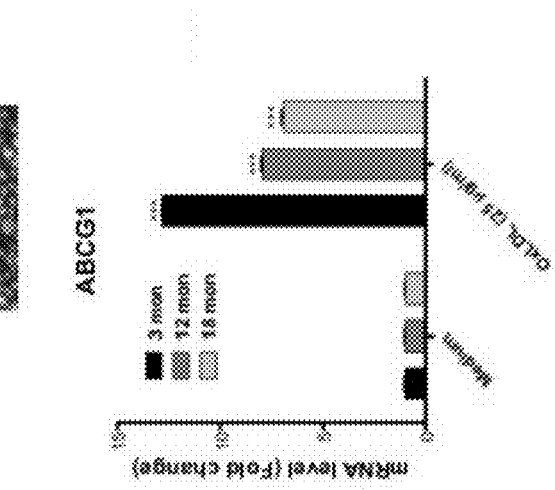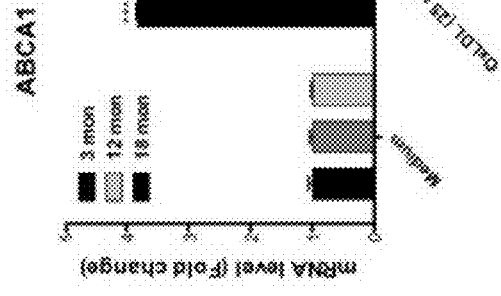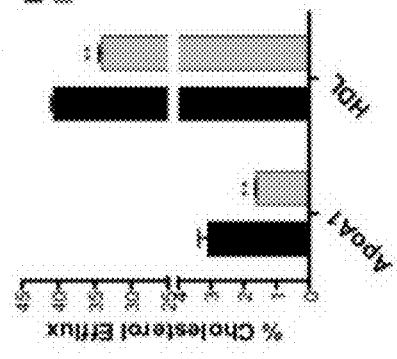

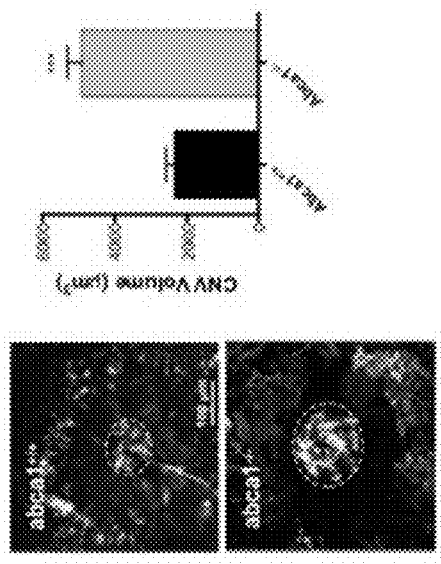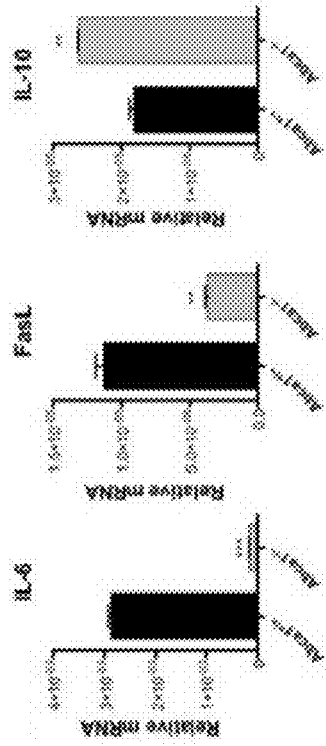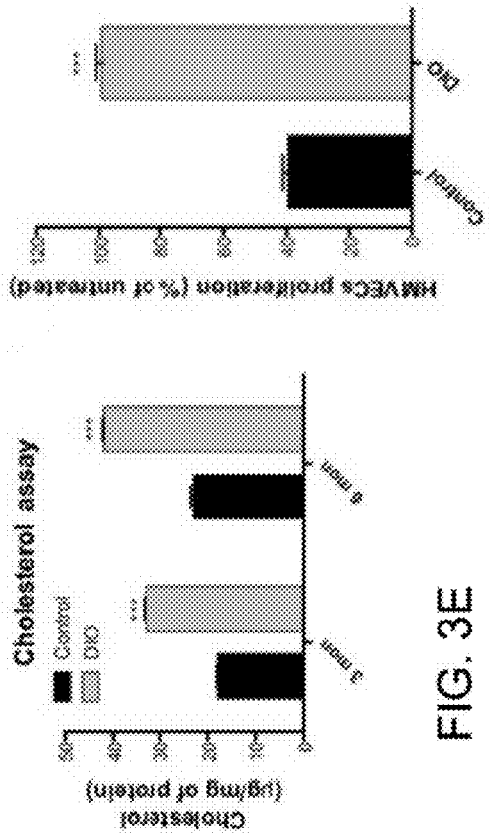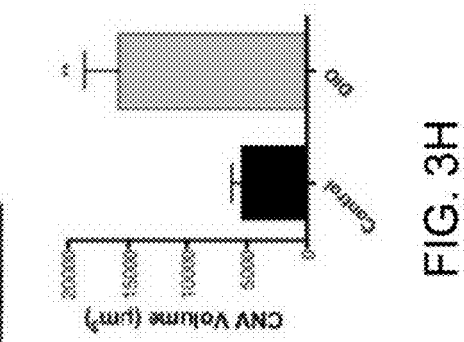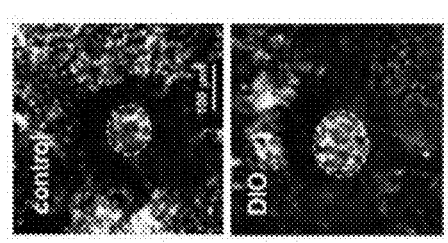

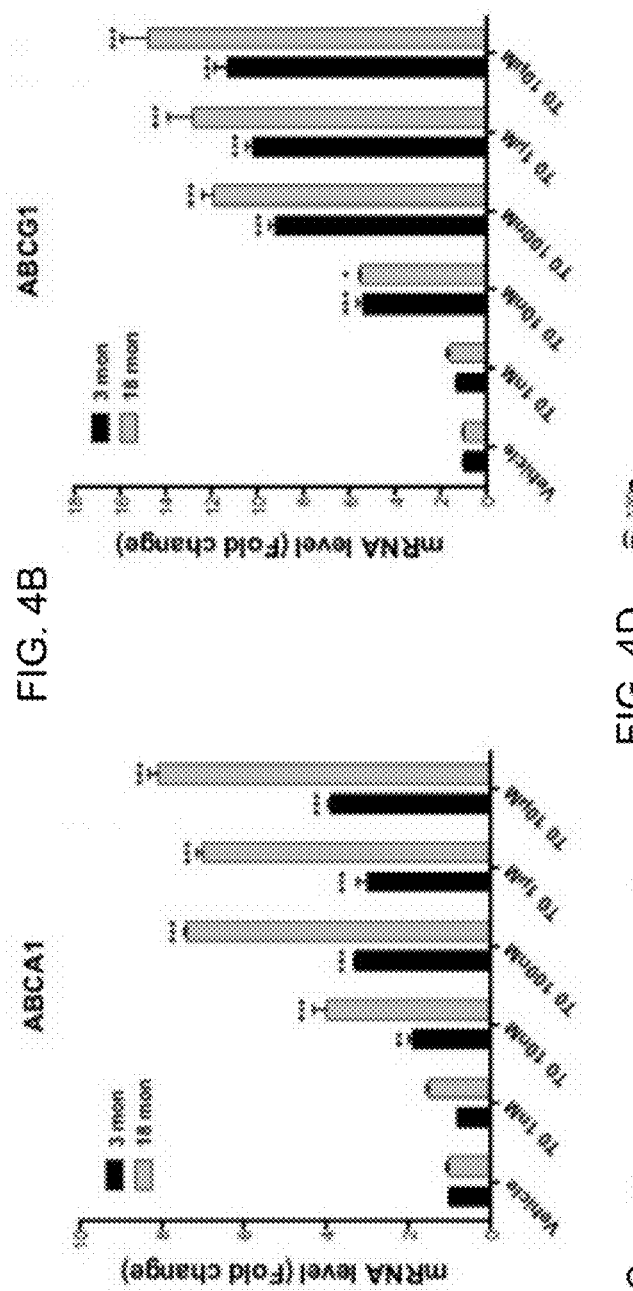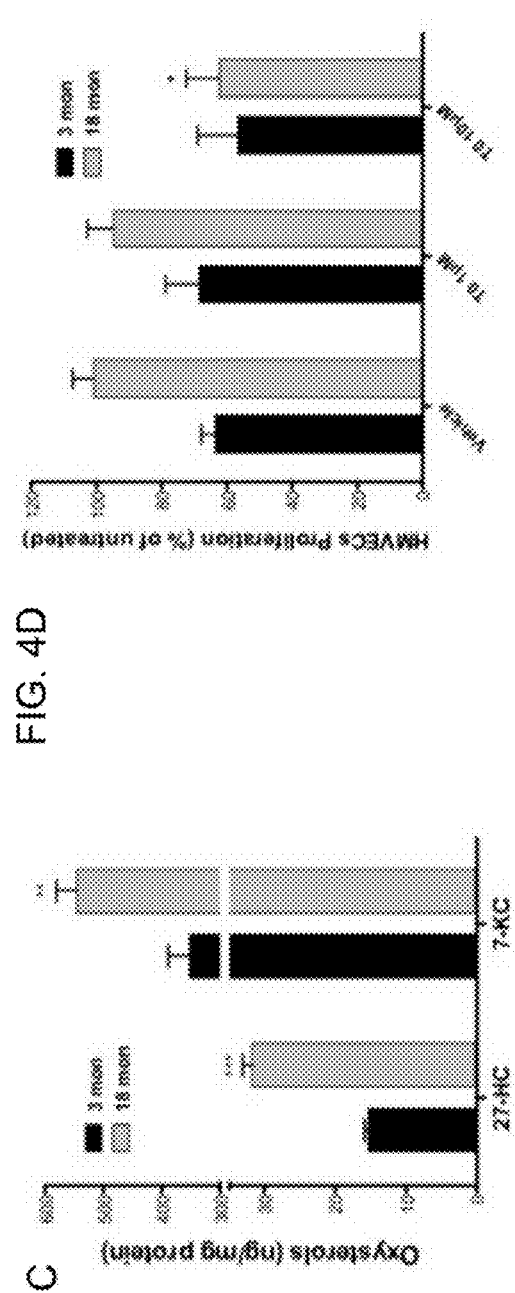

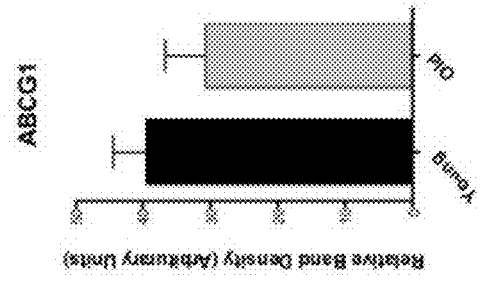
FIG. 5A
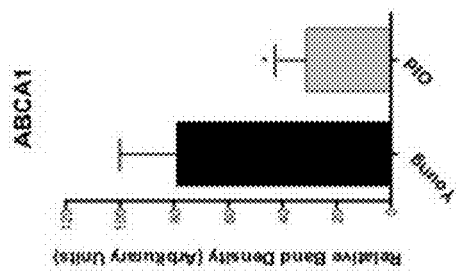
FIG. 5B
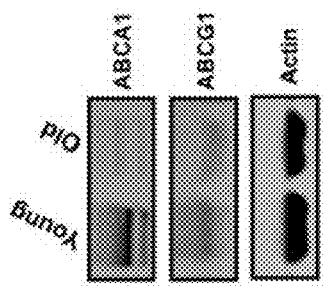
FIG. 5C
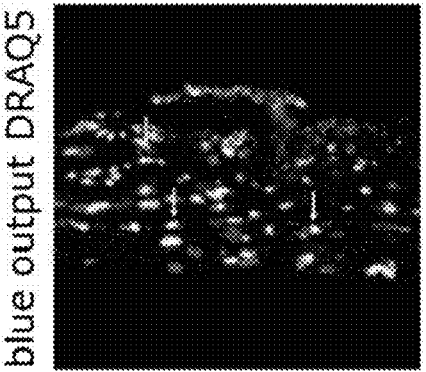
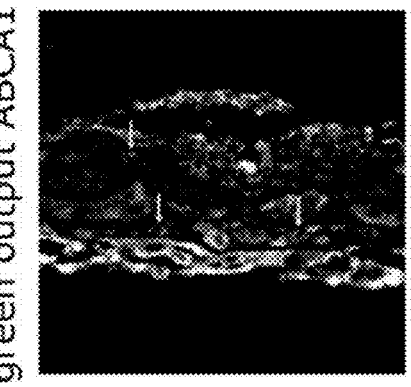
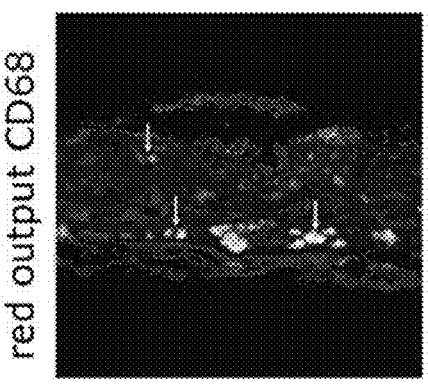
FIG. 5D

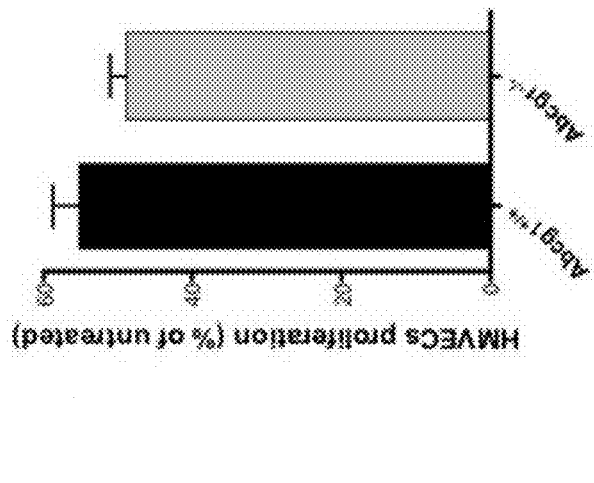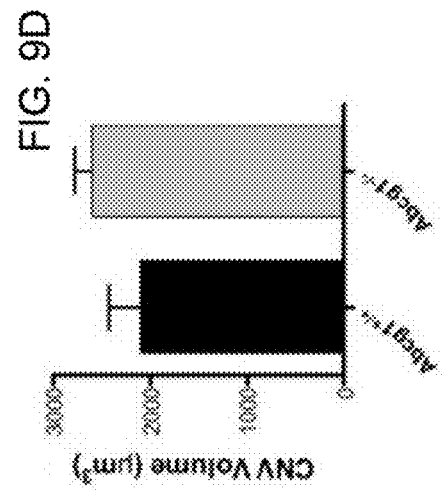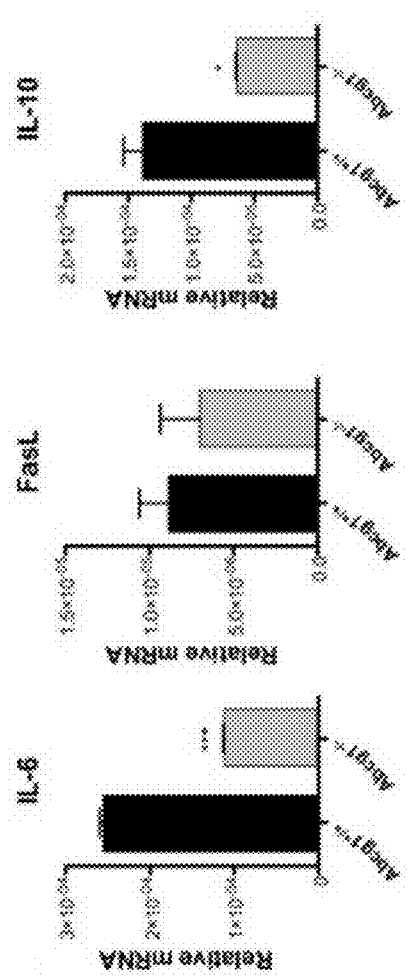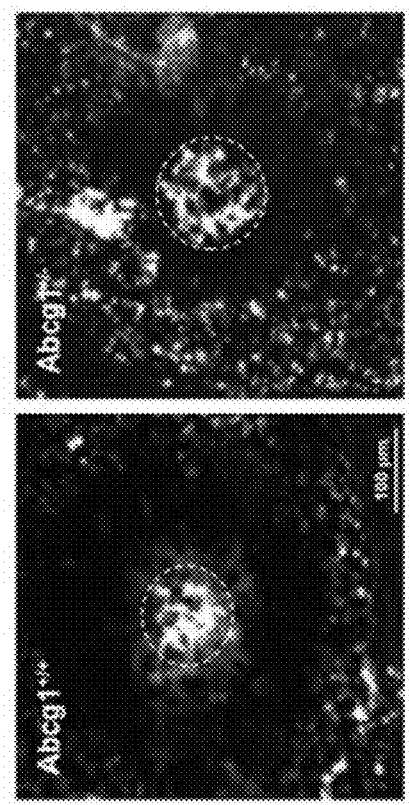
FIG. 9A
FIG. 9B
FIG. 9C
FIG. 9D

FIG. 12

INHIBITION OF CHOROIDAL
NEOVASCULARIZATION

CROSS-REFERENCE TO RELATED
APPLICATIONS

This application is a Divisional of and claims the benefit of and priority to U.S. Non-Provisional patent application Ser. No. 13/918,453, filed Jun. 14, 2013. Application Ser. No. 13/918,453 is a Divisional of Non-Provisional patent application Ser. No. 13/480,024 filed May 24, 2012. Application Ser. No. 13/480,024 claims benefit of and priority to U.S. Provisional Patent Application No. 61/489,656, filed May 24, 2011. These applications are incorporated herein by reference in their entireties.

STATEMENT OF GOVERNMENT SUPPORT

This invention was made with the support of government grant 1R01EY019287-01A1 from the National Institutes of Health. The government of the United States of America has certain rights in this invention.

REFERENCE TO A SEQUENCE LISTING

The Sequence Listing, which is a part of the present disclosure, includes a text file comprising primer nucleotide and/or amino acid sequences of the present invention. The subject matter of the Sequence Listing is incorporated herein by reference in its entirety. The information recorded in computer readable form is identical to the written sequence listing.

INTRODUCTION

There are a number of diseases that include or are characterized by inappropriate or pathological neovascularization. Among these diseases are diseases of the eye, such as diabetic retinopathy, retinopathy of prematurity, and choroidal neovascularization (CNV), i.e., the development of abnormal blood vessels underneath the retina which can occur in age-related macular degeneration (AMD). AMD is the leading cause of blindness and market size is currently about 4-6 billion USD. Only anti-VEGF approaches are currently available and efficacy has plateaued.

AMD includes wet AMD and dry AMD. Blindness in AMD occurs largely from the exudative (wet) form of the disease that is characterized by the development of abnormal blood vessels underneath the retina, also called choroidal neovascularization (CNV) (FIG. 7a, arrows). In wet (exudative) AMD, blood vessels grow up from the choroid behind the retina, and the retina can become detached (FIG. 7a). Senescent macrophages have been shown to polarize to a pro-angiogenic phenotype and promote the development of CNV.

Wet AMD is preceded by non-exudative (dry) AMD. Dry or early AMD is diagnosed by the presence of lipid rich deposits called drusen that develop external to the retinal pigment epithelium (RPE) underneath the retina (FIG. 7b, arrows). In dry (non-exudative) AMD, the retina can also become detached. In the aged eye, alternatively activated macrophages can promote pathologic angiogenesis that can lead to blindness. Drusen are cardinal features of dry AMD. Progression of AMD is often characterized by increased size and number of drusen as well as softening of these deposits with associated detachment of the overlying retinal pigmented epithelium (RPE). Drusen have high lipid content and are rich in both esterified and unesterified cholesterol. These deposits with their high lipid content can serve as a nidus for inflammation. Macrophages have been shown to extend dendritic processes into drusen, and macrophage-mediated inflammation accelerates the development of the wet form of AMD by promoting blinding pathogenic neovascularization. Specifically, programmatic changes in macrophage activation associated with senescence polarize these cells to a proangiogenic or alternatively activated phenotype characterized by increased expression of IL-10 and decreased expression of IL-6 and Fas Ligand (FasL) among others. These alternatively activated macrophages promote the development of CNV that leads to progressive loss of vision. The precise mechanisms by which 'old' macrophages polarize to a pro-angiogenic phenotype are yet unknown.

It has been hypothesized that high-density lipoprotein (HDL) metabolism is associated with CNV/AMD pathogenesis. However, data regarding the association between serum HDL levels and AMD are conflicting (The Eye Disease Case-Control Study Group, Arch. Ophthalmol 110:1701-1708 (1994), van Leeuwen, R., et al., Ophthalmology 111: 1169-1175 (2004); Wachter, A., et al., Ophthalmologe 101: 50-53 (2004); Delcourt, C., et al. Ophthalmic Epidemiol 8: 237-249 (2001); Nowak. M., et al. Clin Exp Med 4: 183-187 (2005); Abalain, J. H., et al., Clin Chim Acta 326: 97-104 (2002); Tan, J. S., et al., Ophthalmology 114: 1143-1150 (2007)). Some studies have shown an inverse relationship with either decreased HDL levels in AMD cases or decreased incidence of advanced AMD with higher HDL (Wachter, A., et al., Ophthalmologe 101: 50-53 (2004); Tan, J. S., et al., Ophthalmology 114: 1143-1150 (2007)).

ABC (ATP binding cassette) transporters are a family of proteins that transport cholesterol out of macrophages and onto extracellular high density lipoprotein (HDL). Of the ABC family of proteins that regulate cholesterol efflux, ABCA1 (ATP binding cassette transporter A1) and ABCG1 (ATP blinding cassette transporter G1) are the most relevant to macrophage cholesterol efflux. ABCA1 promotes cholesterol efflux from cytoplasmic organelles such as lysosomes and the endoplasmic reticulum to the cell surface as well as to lipid poor apolipoproteinA-1 (apoA-1) in the extracellular compartment. ABCA1 regulated efflux of cholesterol out of cells leads to the formation of nascent high density lipoprotein (HDL) particles. ABCG1 can transport cholesterol from the macrophage cell membrane directly to HDL and can contribute to the formation of mature serum HDL.

ABCA1 is the cAMP-inducible apolipoprotein receptor which mediates cholesterol secretion from macrophages (Oram, J. F., et al., J. Biol. Chem. 275: 34508-34511 (2000)). Tserentsoodol, N., et al., *Mol Vis* 12: 1319-1333 (2006) reported that intraretinal lipid transport is dependent on high density lipoprotein-like particles and class B scavenger receptors. Their study reported that ABCA1 as well as apoA1 are localized to the ganglion cell layer, retinal pigment epithelium (RPE), and rod photoreceptor inner segments. Furthermore, they found that lecithin:cholesterol acyltransferase (LCAT), and cholesteryl ester transfer protein (CETP) localizes mainly to the interphotoreceptor matrix (IPM).

Liver X Receptors (LXRs) are nuclear receptors that play a central role in the control of lipid and carbohydrate metabolism as well as inflammation. Through the control of reverse cholesterol transport in macrophages, LXR ligands induce the expression of ABCA1, ABCG1, and ABCG4 transporters. In addition, LXRs promote the transcription of apolipoproteins ApoE and ApoC which act as cholesterol acceptors in macrophages. Moreover, LXRs positively regulate genes involved in lipoprotein remodeling such as lipoprotein lipase, CETP, and the phospholipid transfer protein (Gabbi, C., et al., Molec. Endocrin. 23: 129-136 (2009)).

Tall, A. R., J. Internal Medicine 263 256-273 (2008) reported that plasma HDL levels exhibit an inverse relationship with atherosclerotic cardiovascular disease. This author speculates that the central anti-atherogenic activity of HDL is likely to be its ability to remove cholesterol and oxysterols from macrophage foam cells, smooth muscle cells and endothelial cells in the arterial wall. Furthermore, this author asserts that in cholesterol-loaded macrophages, activation of liver X receptors (LXRs) leads to increased expression of ABCA1, ABCG1 and apoE, and promotes cholesterol efflux. This author further reports that despite some recent setbacks in clinical investigations, there is still interest in therapeutically targeting HDL and macrophage cholesterol efflux pathways affecting atherosclerotic cardiovascular disease, via treatments with niacin, cholesterol ester transfer protein inhibitors, LXR activators and infusions of apoA-1, phospholipids and peptides.

Cholesteryl ester transfer protein (CETP) is a plasma glycoprotein involved in reverse cholesterol transport (RCT), i.e., the transfer of cholesteryl esters from HDL to low density lipoprotein cholesterol (LDL) and very low density lipoprotein cholesterol (VLDL) (van der Velde. A., World J. Gastroenterol. 16(47): 5908-5915 (2010)). CETP activity can lead to lower levels of HDL while raising the levels of proatherogenic LDL and VLDL. CETP deficiencies in human populations have been associated with high levels of serum HDL. CETP is believed to influence macrophage cholesterol efflux indirectly by regulating the serum levels and stability of HDL particles. It is hypothesized to do so by facilitating the transport of cholesterol esters (CE) from HDL particles to low density lipoproteins (LDL) and very low density lipoproteins (VLDL) and in turn transporting triglycerides to HDL. The end result of this exchange can be the generation of unstable HDL. In macrophages from conditional ABCA1$^{-/-}$ mice lacking the gene and protein only within macrophages, there is accumulation of free cholesterol (FC) within these cells. Intracellular accumulation of cholesterol at baseline and after stimulation of macrophages is also associated with increased lipid rafts in the plasma membrane and polarization of macrophages to a pro-inflammatory phenotype.

While inhibition of CETP is considered a potential approach to treat atherosclerotic cardiovascular disease, negative phase III studies on clinical endpoints with the CETP inhibitor torcetrapib challenge the future perspectives of CETP inhibitors as potential therapeutic agents (Weber, O., et al., Cell. Mol. Life Sci. 67: 3139-3149 (2010)). However, these studies involve systemic administration of CETP inhibitors.

Genome wide association studies (GWAS) have identified single nucleotide polymorphisms (SNPs) in the innate immune system, specifically in the complement regulatory pathway that correlate with increased the risk of development and progression of AMD. GWAS have also demonstrated an association between SNPs in genes involved in cholesterol metabolism and advanced AMD. These include ABCA1, cholesterol esteryl transferase protein (CETP), hepatic triglyceride lipase C (LIPC) and lipoprotein lipase (LPL). Multivariate analyses have shown that allelic associations with advanced AMD are independent of actual serum HDL or lipid levels. It is thus apparent that the biologic pathways that connect macrophage-mediated inflammation, cholesterol regulation and age in AMD are highly complex and cannot be explained by a simple association of increased risk and abnormal serum lipid component levels.

An analysis of SNPs by Chen, W., et al. (Proc. Nat'l Acad. Sci. USA 107: 7401-7406 (2010)) identified a susceptibility locus for AMD near TIMP3. In addition, their data revealed strong association signals with alleles at two loci: hepatic lipase (LIPC) and CETP. These loci were previously associated with high-density lipoprotein cholesterol (HDL-c) levels in blood. Consistent with a hypothesis that high-density lipoprotein (HDL) metabolism is associated with AMD pathogenesis, these workers observed an association with AMD of HDL-c-associated alleles near lipoprotein lipase (LPL) and ABCA1 genes.

An analysis of SNPs by Neale, B. M., et al. (Proc. Nat'l Acad. Sci. USA 107: 7395-7400 (2010)) reported a significant association between advanced AMD and the hepatic lipase gene (LIPC) locus in their genome-wide association study. However, these workers found that previously reported results from HDL loci was inconsistent with a straightforward correlation between HDL levels and AMD. Data from their study suggested to these authors that the HDL-raising alleles of ABCA1 and CETP may increase the risk of AMD, although they did not consider their results as currently genome-wide significant. Thus, they concluded that the association between advanced AMD and LIPC may not represent a phenotypic correlation to, or a causal effect of, serum HDL but could indicate a shared underlying biologic mechanism involving the cholesterol pathway.

An analysis of single-nucleotide polymorphisms ("SNPs") by Yu, Y. et al., Invest Ophthalmol Vis Sci. 2011 Mar. 29. [Epub ahead of print] indicated that loci LIPC and ABCA1 are related to intermediate and large drusen as well as advanced AMD. While Yu et al. report an inverse association between LIPC and ABCA1 with drusen, they speculate that is possible that functional variants regulating expression levels of LIPC and ABCA1 may promote cholesterol efflux, reduce the activation of the inflammatory pathway in subretinal macrophages and result in less drusen accumulation. Yu et al. further state that there is an allele in ABCA1 which decreases HDL levels and an allele in LIPC which increases HDL levels, and that both alleles are associated with decreasing risk of advanced AMD and drusen.

There is no prior evidence that cholesterol regulation within macrophages affects angiogenesis within the eye and can affect outcomes in age-associated eye disease. There are currently no approaches that target cholesterol efflux as a mechanism to prevent blindness from wet AMD. The above-cited references do not teach that increasing cholesterol efflux from macrophages in the eye would provide an effective method of treating an ocular disease characterized by choroidal neovascularization such as AMD, nor do they teach that increasing ABC transporter expression or activity would provide an effective method of treating an ocular disease characterized by choroidal neovascularization such as AMD.

SUMMARY

The present inventor has demonstrated that as macrophages age, their ability to efflux cholesterol from the intracellular space declines. By using both gain of function and loss of function experiments, he has demonstrated that upregulation of the ABCA1 transporter protein on macrophages can alter macrophage polarization and protect against choroidal neovascularization (CNV) and blindness in age-associated eye disease.

Macrophages from old mice have reduced ABC transporter expression, at the levels of both gene and protein expression, and can be unable to regulate CNV in eyes, unlike macrophages from young mice. In some configurations of the present teachings, treating old macrophages with agonists (LXR1) that can increase ABCA1 expression can alter macrophage activation and can restore their ability to regulate CNV.

In some configurations, knockout mouse models of AMD, treatment with agonists that increase ABCA1, loss of function and gain of function experiments demonstrated the protective role of elevating ABCA1 in regulating angiogenesis in eye disease, and human data from patients and controls were used to demonstrate the translation of mouse findings in human disease. In some embodiments, simultaneous treatment with a PPAR agonist and LXR agonist (oxysterol) can have an additive effect on ABCA1 expression.

The present teachings disclose methods of treating an ocular disease characterized by choroidal neovascularization (CNV) in a subject in need thereof. In some configurations, the methods comprise administering to the subject a therapeutically effective amount of an activator of an ATP-binding cassette (ABC) transporter. As used herein, an activator of an ABC transporter can be a compound that directly or indirectly increases expression or activity of an ABC transporter, such as, for example, an agonist for PPARα, PPARγ, or PPARδ (Borst, P., et al., Ann. Rev. Biochem. 71: 537-592 (2002); Chinetti, G., et al., Nat. Med. 7: 53-58 (2001); Oliver, W. R. J., et al., Proc. Nat'l. Acad. Sci. USA 98: 5306-5311 (2001) or an LXR agonist. In various configurations, the ABC transporter can be selected from the group consisting of ABCA1, ABCG1, and a combination thereof.

In various embodiments, the activator of an ATP-binding cassette (ABC) transporter can be a compound that increases ABCA1 expression described in U.S. Pat. No. 7,579,504, U.S. Pat. No. 7,423,045, or U.S. Pat. No. 7,666,900. In various embodiments, the activator of an ATP-binding cassette (ABC) transporter can be an LXR agonist. In various embodiments, the LXR agonist can be selected from the group consisting of TO-901317 (CAS #: 293754-55-9; Synonym: N-(2,2,2-trifluoro-ethyl)-N-[4-(2,2,2-tri-fluoro-1-hydroxy-1-trifluoromethyl-ethyl)-phenyl]-benzenesulfonamide), N,N-dimethyl-3beta-hydroxy-cholenamide (DMHCA), methyl-3β-hydroxy-5α,6α-epoxycholanate (Yan, W., et al., Pharmacology 86: 306-312 (2010)), and GW3965 (2-[3-[3-[[2-chloro-3-(trifluoromethyl)phenyl]methyl-(2,2-diphenyl-ethyl)amino]propoxy]phenyl]acetic acid).

In various embodiments, the administering a therapeutically effective amount of an activator of an ABC transporter can comprise administering the activator intraocularly, periocularly or systemically. In various embodiments, the administering a therapeutically effective amount of an activator of an ABC transporter comprises administering to an eye of the subject a pharmaceutically acceptable eye drop formulation comprising the activator. In various embodiments, the administering a therapeutically effective amount of an activator of an ABC transporter comprises intraocularly can comprise injecting into an eye of a subject in need a pharmaceutically acceptable formulation comprising the activator. In some embodiments, the administering a therapeutically effective amount of an activator of an ABC transporter comprises administering the activator orally or parenterally in a pharmaceutically acceptable formulation.

In various embodiments, the disease can be age-related macular degeneration (AMD). In various embodiments, the disease can be diabetes. In various embodiments, the disease can be a retinopathy of prematurity.

In some configurations the methods comprise administering to a subject in need of treatment a therapeutically effective amount of an inhibitor of cholesteryl ester transfer protein (CETP) activity. In various embodiments, the inhibitor of CETP activity can be selected from the group consisting of Torcetrapib, Anacetrapib and Dalcetrapib.

In some embodiments, the administering a therapeutically effective amount of an inhibitor of CETP activity can comprise administering the inhibitor intraocularly. In various embodiments, the administering a therapeutically effective amount of an inhibitor of CETP activity can comprise administering to an eye of the subject a pharmaceutically acceptable eye drop formulation comprising the inhibitor. In some embodiments, the administering a therapeutically effective amount of an inhibitor of CETP activity can comprise intraocularly injecting a pharmaceutically acceptable formulation comprising the inhibitor. In various embodiments, the administering a therapeutically effective amount of inhibitor of CETP activity can comprise administering the inhibitor orally or parenterally in a pharmaceutically acceptable formulation.

In some configurations a method of the present teachings can comprise administering to a subject in need thereof a therapeutically effective amount of an inhibitor of cholesteryl ester transfer protein (CETP) gene expression.

In various embodiments, the inhibitor of CETP gene expression can be an inhibitory RNA. In some embodiments, the inhibitory RNA can be an siRNA. In various embodiments, the inhibitor of CETP gene expression can be an inhibitory RNA. In some embodiments, the inhibitory RNA can be an miRNA.

In various embodiments, the administering a therapeutically effective amount of an inhibitor of CETP gene expression can comprise administering the inhibitor intraocularly or periocularly. In some embodiments, the administering a therapeutically effective amount of an inhibitor of CETP gene expression can comprise administering to an eye of the subject a pharmaceutically acceptable eye drop formulation comprising the inhibitor. In various embodiments, the administering a therapeutically effective amount of an inhibitor of CETP gene expression can comprise intraocularly injecting a pharmaceutically acceptable formulation comprising the inhibitor. In various embodiments, the administering a therapeutically effective amount of an inhibitor of CETP gene expression can comprise administering the inhibitor orally or parenterally in a pharmaceutically acceptable formulation.

In some configurations the methods can comprise, in order: a) providing a cell culture comprising macrophages; b) adding an activator of an ATP-binding cassette (ABC) transporter to the culture in an amount sufficient to stimulate ABC transporter expression and/or activity in the macrophages; and c) administering the macrophages to the subject.

In some embodiments, the activator of an ATP-binding cassette (ABC) transporter can be an LXR activator. In various embodiments, the LXR activator can be N-(2,2,2-trifluoro-ethyl)-N-[4-(2,2,2-tri-fluoro-1-hydroxy-1-trifluoromethyl-ethyl)-phenyl]-benzenesulfonamide (CAS #: 293754-55-9). In various embodiments, the activator of an ATP-binding cassette (ABC) transporter can be a compound that increases ABCA1 expression described in U.S. Pat. No. 7,423,045. In various embodiments, the activator of an ATP-binding cassette (ABC) transporter can be an LXR agonist. In some embodiments, the LXR agonist can be selected from the group consisting of TO-901317 (CAS #: 293754-55-9; Synonym: N-(2,2,2-trifluoro-ethyl)-N-[4-(2,2,2-tri-fluoro-1-hydroxy-1-trifluoromethyl-ethyl)-phenyl]-benzenesulfonamide), methyl-3β-hydroxy-5α,6α-epoxycholanate (Yan, W., et al., Pharmacology 86: 306-312 (2010)), GW3965 (2-[3-[3-[[2-chloro-3-(trifluoromethyl)phenyl]methyl-(2,2-diphenyl-ethyl)amino]propoxy]phenyl]acetic acid).

In various embodiments, the providing a cell culture comprising macrophages comprises providing a cell culture comprising peripheral blood mononuclear cells (PBMCs). In some embodiments, the cell culture comprising PBMCs can comprise PBMCs autologous to the subject. In various embodiments, the providing a cell culture comprising macrophages can comprise growing macrophages comprised by the culture by methods known to skilled artisans, for example by the method of Bennett, S., et al., J. Immunol. Methods 153: 201-2-2 (1992).

In some embodiments, the administering the macrophages to the subject can comprise administering the macrophages to the subject intravenously. In various embodiments, the administering the macrophages to the subject can comprise administering the macrophages to the subject periocularly. In various embodiments, the administering the macrophages to the subject comprises administering the macrophages to the subject intraocularly.

In some embodiments, the present teaching include methods of treating an ocular disease characterized by choroidal neovascularization (CNV), comprising administering to a subject in need thereof a therapeutically effective amount of an inhibitor of miR33, such as, without limitation, a single-stranded RNA which specifically inhibits endogenous miR33 expression. In some configurations, the administering the inhibitor of miR33 can inhibit vascular endothelial cell proliferation.

BRIEF DESCRIPTION OF THE DRAWINGS

FIG. 1A-F illustrate age-associated decrease in gene expression of ABC transporters (ABCA1 and ABCG1) in senescent macrophages.

FIG. 2A-G illustrate age associated impairment in macrophage cholesterol efflux capacities.

FIG. 3A-H illustrate that the ability of macrophages to regulate vascular proliferation is altered by Abca1 deletion or cholesterol-rich diet.

FIG. 4A-I illustrate that LXR agonist treatment restores the functional capacities of senescent macrophages.

FIG. 5A-D illustrate age-related alteration of ABCA1 expression in human PBMCs.

FIG. 9A-D illustrate that the deletion of Abcg1 has no effect on macrophage-mediated regulation of vascular proliferation.

FIG. 12 illustrates Abca1 and Abcg1 promoter methylation in young and old macrophages.

DETAILED DESCRIPTION

Figure 4E:
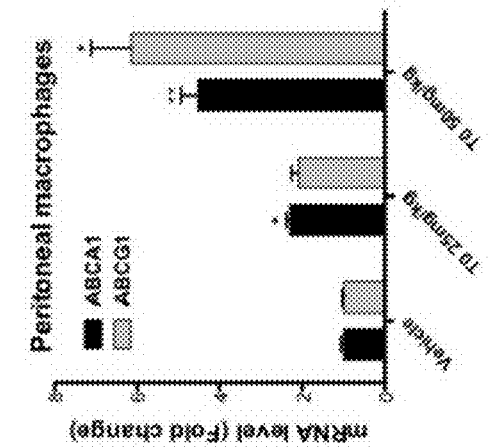
Figure 4F:
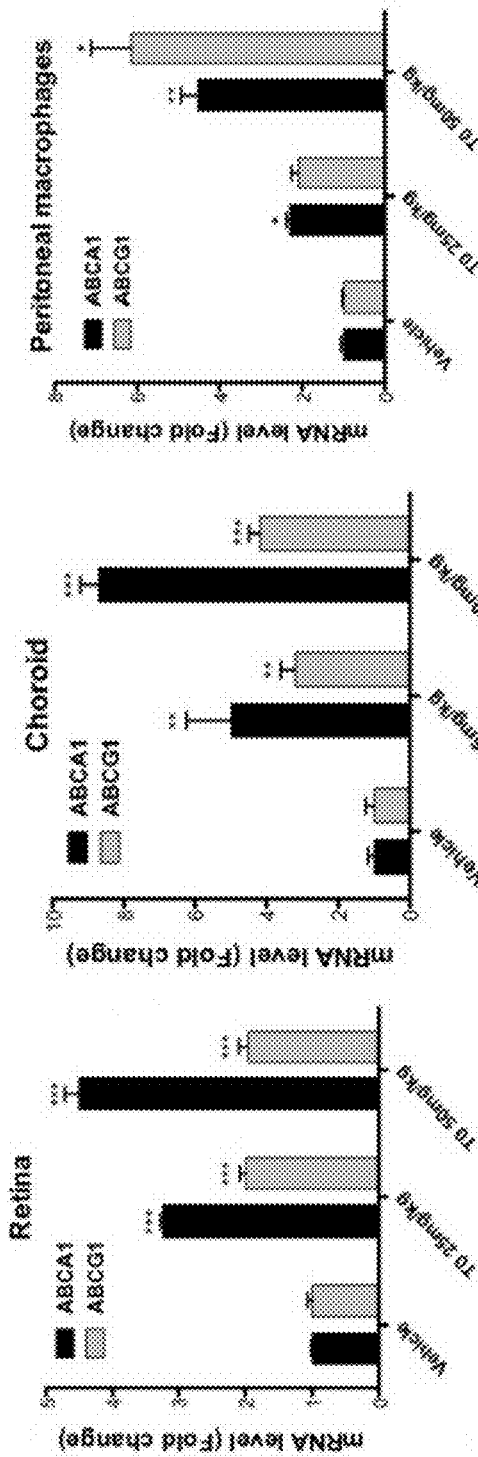
Figure 4G:
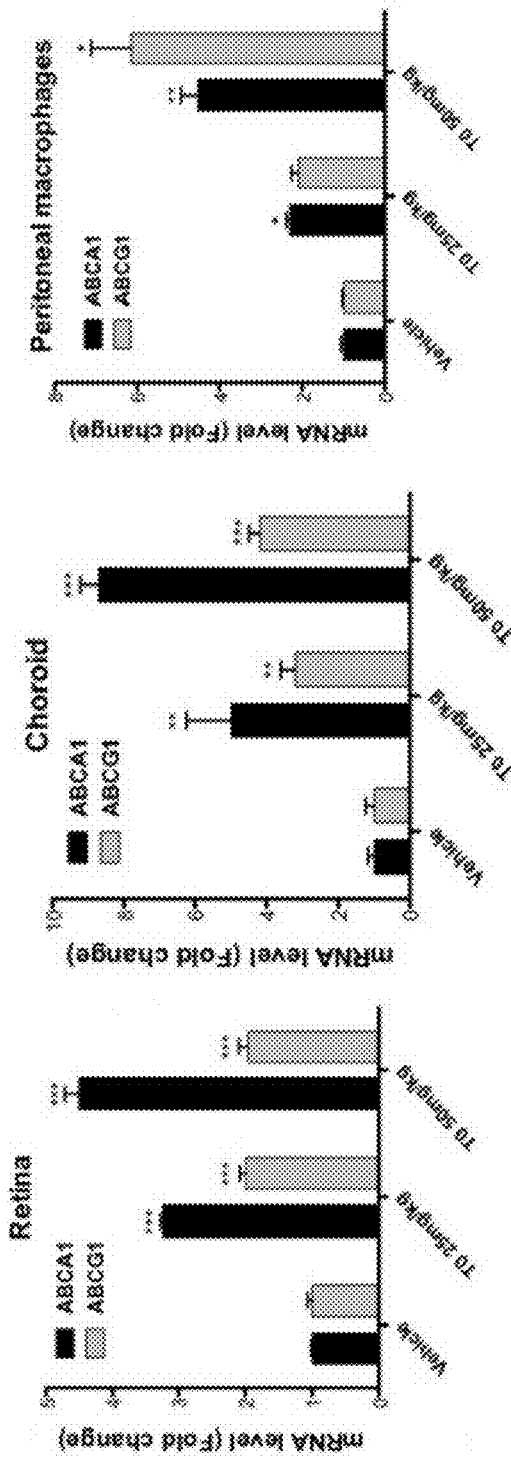

The present inventors have demonstrated that the cholesterol efflux regulators ABCA1 and ABCG1 are downregulated in macrophages with age in both mice and human. Age-associated downregulation of ABCA1 leads to alternative pro-angiogenic polarization of macrophages to an M2-like disease promoting phenotype. This is especially interesting in the light of previous studies that have shown that older mice have significantly higher volumes of CNV (Kelly, J., et al., *J. Clin. Invest.* 117, 3421-3426, 2007) after injury and that advanced AMD) (van Leeuwen, R., et al., Epidemiology of age-related maculopathy: a review. *Eur. J. Epidemiol.* 18, 845-854, 2003) characterized by CNV only develops in individuals over 50 years of age. Using loss of function experiments with knockout mice, we have been able to demonstrate that macrophages deficient in ABCA1 are unable to regulate CNV in vivo and vascular endothelial cell proliferation in vitro. In essence, Abca1$^{-/-}$ macrophages functionally behave like senescent macrophages isolated from mice at least 18 months of age. Of interest, loss of Abcg1 does not seem to affect the ability of these cells to regulate CNV or vascular endothelial proliferation suggesting a dominant role for ABCA1 in this process. A potential reason for the ABCA1 dominance in this process is the complete polarization of Abca1$^{-/-}$ macrophages to an M2 phenotype identical to that seen in senescent macrophages that are unable to regulate aberrant angiogenesis. By contrast, Abcg1$^{-/-}$ macrophages have a mixed phenotype, which may explain why they retain their functional abilities and do not demonstrate a programmatic shift to a senescent phenotype. It is also possible that ABCA1-driven efflux of intracellular cholesterol to the cell surface prior to deposition on to lipid-poor ApoA-1 is the critical pathway involved in the ability of macrophages to regulate aberrant and proliferative angiogenesis.

Experiments in DIO mice have also provided insights in to the effects of cholesterol loading on macrophage function in the eye. Macrophages fed a high fat diet for a period of up to 6 months are unable to regulate CNV in vivo and vascular endothelial cell proliferation in vitro. These findings shed light on conflicting data from genetic and epidemiologic studies that demonstrate a complex association between polymorphisms in genes that regulate HDL and cholesterol metabolism and AMD as outlined above (Chen, W. et al. Genetic variants near TIMP3 and high-density lipoprotein-associated loci influence susceptibility to age-related macular degeneration. *Proc Natl Acad Sci USA* 107, 7401-7406, 2010; Neale. B. M. et al. Genome-wide association study of advanced age-related macular degeneration identifies a role of the hepatic lipase gene (LIPC). *Proc. Natl. Acad. Sci. USA* 107, 7395-7400, 2010). The data from knockout mice and the reduced expression of ABC transporters from old humans, diagnosed with AMD, suggest that local regulation of cholesterol efflux in the eye and the ability of macrophages to efficiently transport cholesterol from drusen to HDL and on to the systemic circulation are critical for the prevention of triggering of drusen-induced CNV in AMD. In older animals and humans, macrophages lose their ability to efflux cholesterol efficiently. This leads to alternative pro-angiogenic polarization of these cells, which in the appropriate genetic context of polymorphisms in complement regulatory genes (Edwards, A. O. et al. Complement factor H polymorphism and age-related macular degeneration. Science 308, 421-424, 2005) and alongside environmental cues such as smoking, can create a lethal micromilieu for the development and progression of advanced AMD where new blood vessels proliferate, cause bleeding and induce the formation of scar tissue that leads to photoreceptor loss and blindness. Our gain of function studies demonstrate that by upregulating ABC transporter expression in senescent macrophages using LXR agonists, we are able to restore their ability to inhibit vascular endothelial cell proliferation and CNV. In essence, LXR agonists are able to reverse the senescent phenotype and restore their angioregulatory function to levels comparable to mice that are significantly younger.

Our work also reveals that upregulation of miR33 in aged macrophages might be responsible for the repression of ABCA1 that leads to defective cellular cholesterol metabolism in senescent macrophages. Indeed, antagonism of endogenous miR33 improves macrophage regulation of vascular proliferation.

These results have significant therapeutic implications. CNV in AMD accounts for a large majority of blindness from this disease. Therapeutic intervention prior to the development of advanced disease with effective agents that upregulate macrophage cholesterol efflux in the eye can prevent progression and can be used as prophylaxis against the development of CNV and its blinding complications. The ability to deliver such therapies locally to the eye is a unique advantage in this immune privileged organ (Niederkorn, J. Y. See no evil, hear no evil, do no evil: the lessons of immune privilege. Nat. Immunol. 7, 354-359, 2006) and can be an effective barrier to off-target complications that are often seen with systemic therapy.

Methods and compositions described herein utilize laboratory techniques well known to skilled artisans. Such techniques can be found in laboratory manuals such as Sambrook, J., et al., Molecular Cloning: A Laboratory Manual, 3rd ed. Cold Spring Harbor Laboratory Press, Cold Spring Harbor, N.Y., 2001; Spector, D. L. et al., Cells: A Laboratory Manual, Cold Spring Harbor Laboratory Press, Cold Spring Harbor, N.Y., 1998; Harlow, E., Using Antibodies: A Laboratory Manual, Cold Spring Harbor Laboratory Press, Cold Spring Harbor, N.Y., 1999; and Sioud, M., ed. Ribozymes and siRNA Protocols, New York, Springer-Verlag, 2004; Sohail, M., ed., Gene Silencing by RNA Interference: Technology and Application. CRC Press LLC, Boca Raton, Fla., 2005; Schepers, U., RNA Interference in Practice: Principles, Basics, and Methods for Gene Silencing in *C. elegans, Drosophila*, and Mammals, Wiley-VCH Verlag GmbH & Co., Weinheim 2005; and Engelke. D., RNA Interference (RNAi) Nuts & Bolts of RNAi Technology. DNA Press LLC, 2003. Methods of administration of pharmaceuticals and dosage regimes, can be determined according to standard principles of pharmacology well known skilled artisans, using methods provided by standard reference texts such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003. Other techniques can be found in the references cited herein. In addition, the Examples may make use of the following materials and methods.

Whole blood can be drawn from subjects by venipuncture using standardized phlebotomy procedures into 8-mL green-capped Vacutainers containing the anti-coagulant sodium heparin (Becton Dickinson, Franklin Lakes, N.J.). Plasma can be collected by centrifugation, aspirated and stored at −80° C. for later use. The plasma can be replaced with PBS and the blood resuspended and further diluted with an equal volume of PBS. PBMCs can be isolated by layering the diluted blood onto Ficoll-Paque PLUS (GE Healthcare), centrifuging for 22 min at 800 g, aspirating the PBMC layer and washing it once in PBS. The PBMCs (approximately $2 \times 10^7$ cells) can be centrifuged at 500 g for 7 min and either stored as frozen unactivated cells in 90% FBS and 10% DMSO at −80° C. for further culture and analysis or resuspended in TRIzol (Invitrogen, Grand Island, N.Y.) and stored at −80° C. for DNA and RNA extraction and analysis.

Isolation, Separation and Culture of Primary Cells. Leukopaks of peripheral blood from subjects can be collected according to standard methods, such as a National Institutes of Health Clinical Center protocol NCT00001846. A subject's peripheral blood and plasma samples can be frozen according to standard methods. Mononuclear leukocytes can be isolated by Ficoll-Hypaque gradient centrifugation. The light density fraction (buffy coat) can be collected, and washed, for example twice with PBS. PBMC can be activated, e.g., by 1 μg/mL PHA (Abbott Diagnostics, Abbott Park, Ill.) and the cells can be cultured with 20 units/mL of IL-2 (Zeptometrix, Buffalo, N.Y.), M-CSF or GM-CSF and subcultured, e.g., every 3-5 days. For enrichment or isolation of macrophages, other cells can be removed using magnetic activated cell sorting (MACs) methods according to manufacturer's instructions (Miltenyi Biotec, Inc., Auburn, Calif.) and antibodies against cell-surface antigens not found on macrophages. After isolation or enrichment, macrophages can be cultured using a standard culture medium such asn RPMI-1640 medium supplemented with 10% fetal calf serum (FCS), 2 mM glutamine, 1 mM sodium pyruvate and antibiotics.

Animals

CS7BL/6 mice (age <6 months), Diet Induced Obese mice (DIO) and age-matched controls were purchased from The Jackson Laboratory. C57BL/6 old mice (age >18 months) were purchased from National Institute of Aging. Macrophage-specific ABCA1 knockout mice (Abca1−/−) were generated by breeding Abca1flox/flox mice, provided by Dr. John S Parks (Timmins, J. M. et al. Targeted inactivation of hepatic Abca1 causes profound hypoalphalipoproteinemia and kidney hypercatabolism of apoA-I. J Clin Invest 115, 1333-1342, 2005) with Lys-M Cre mice (The Jackson Laboratory, Bar Harbor, Me.). Previously characterized Abcg1−/− knockout mice (Baldan, A. et al. Deletion of the transmembrane transporter ABCG1 results in progressive pulmonary lipidosis. J. Biol. Chem. 281, 29401-29410, 2006); Kennedy, M. A. et al. ABCG1 has a critical role in mediating cholesterol efflux to HDL and preventing cellular lipid accumulation. Cell Metab. 1, 121-131, 2005) were provided by Dr. Angel Baldan.

Cells

Splenic macrophages were isolated by positive selection as previously described (Apte, R. S., et al., Macrophages Inhibit Neovascularization in a Murine Model of Age-Related Macular Degeneration. PLoS Med 3(8): e310, doi:10.1371/journal.pmed.0030310 2006). In brief, F4/80+ macrophages were purified from dissociated mouse spleen using magnetic separation (Stemcell Technologies Inc., Vancouver, BC Canada). Flow cytometry analysis of selected cell demonstrated cell purity greater than 90%.

Peritoneal macrophages recruitment was elicited by intraperitoneal injection of 4% thioglycollate. Five days after injection, macrophages were harvested and cultured in RPMI⁻¹ 1640 overnight (Gibco, Grand Island, N.Y.). Macrophages were then washed with RPMI-1640 and non-adherent cells removed.

Young or old mouse peripheral blood mononuclear cells (PBMCs) were prepared by centrifugation over Histopaque 1083 (Sigma-Aldrich) according to the manufacturer's instructions.

Figure 13:
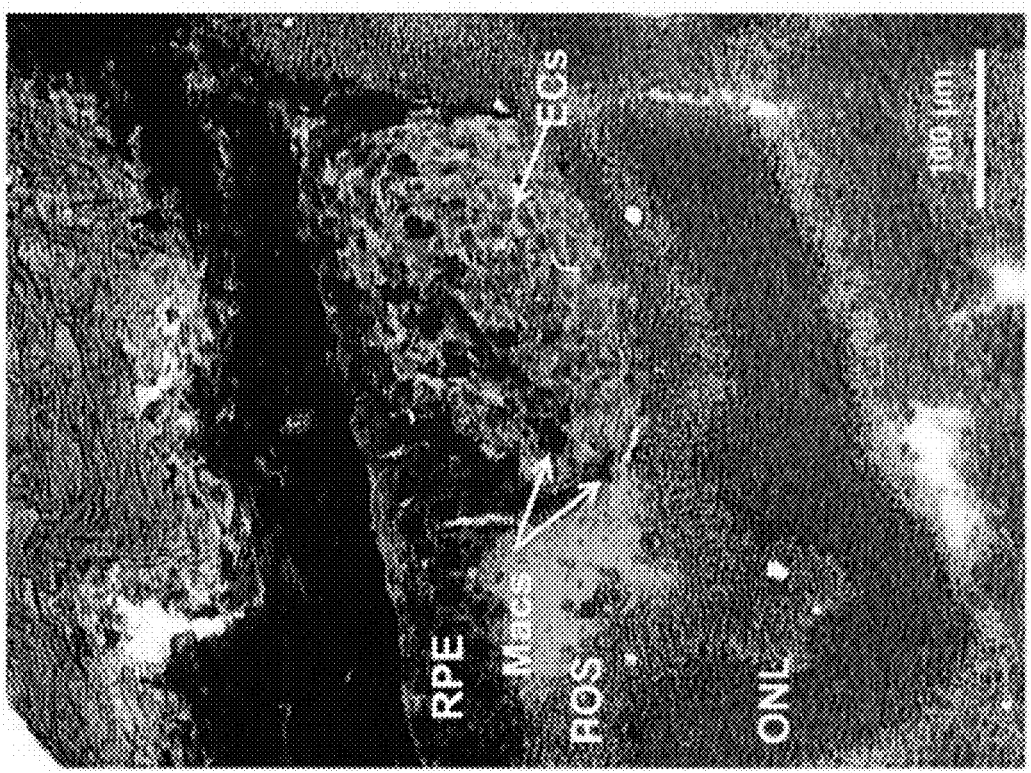
FIG. 13 illustrates the CNV complex. Cryostat section of eye with CNV and stained for H&E.

Eye macrophages were isolated from CNV complexes by laser capture microdissection. Seven days after laser induction of CNV, mice were euthanized in a CO2 chamber, and their eyes were harvested for tissue processing. Eyes were cryoprotected in 1.5% sucrose, embedded in Tissue-Tek OCT compound (Sakura Finetek USA) and frozen. Cryostat sections, 12 μm thick, were mounted on PEN-Membrane slides (Leica Microsystems Inc., Buffalo Grove, Ill.). Sections were then incubated in absolute ethanol and briefly stained for H&E (FIG. 13). In FIG. 13, RPE: Retinal Pigment Epithelium; Macs: Macrophages; POS: Photoreceptors Outer Segments; ONL: Outer Nuclear Layer; ECs: Endothelial Cells. Scale bar, 100 μm. Single macrophages in CNV complexes were collected using Laser Microdissection System LMD6000 (Leica). Total RNA was extracted using the RNeasy mini kit (Qiagen). Human dermal microvascular endothelial cells (HMVECs) were purchased from Lonza (Basel, Switzerland) and cultured in EGM2V media.

Human peripheral blood mononuclear cells were isolated from young (age range 25-34 years, n=9) or old (age range 67-87 years, n=9) donors diagnosed with neovascular AMD. This study was approved by the Human Research Protection Office of Washington University in St. Louis School of Medicine, and informed consent was obtained from all blood donors. PBMCs were purified by density gradient centrifugation using BD Vacutainer CPT according to the manufacturer's instructions (Becton Dickinson, Franklin Lakes, N.J.). PBMCs were resuspended and cultured in RPMI-1640 for 1 h and non-adherent cells were washed out.

Real-Time PCR and Gene Expression Analysis

Total RNA was prepared from splenic macrophage, peritoneal macrophages, retina, choroid or PBMCs using the RNeasy mini kit (Qiagen Inc., Valencia, Calif.). cDNA was prepared using the High Capacity cDNA Archive Kit (Applied Biosystems) and PCR amplifications of cDNA were performed using Taqman probe-based gene expression assay (Applied Biosystems) as previously described (Kelly, J., et al., Senescence regulates macrophage activation and angiogenic fate at sites of tissue injury in mice. J Clin Invest 117, 3421-3426, 2007). Primer and probe sets were as follows: ActB, Mm00607939_s1; ABCA1, Mm00442649_m1; ABCG1, Mm01348250_m1; IL-6, Mm00446190_m1; FasL, Mm00438864_m1; IL-10, Mm99999062_m1; 18s rRNA, Hs99999901_s1; ABCA1, Hs00442663_m1; ABCG1: Hs 01555199_g1; IL10, Hs00961622_m1.

Western Blot Analysis

Whole cell lysate was extracted from mouse peritoneal macrophages or human PBMCs using lysis buffer (50 mM Tris (pH=7.4), 150 mM NaCl, 1% EDTA, 10% TritonX, and 1% SDS) with proteinase inhibitor (Complete, Roche). 20 mg lysates were resolved using NuPAGE gradient gels (Invitrogen) and electro-transferred to nitrocellulose membranes (Whatman) according to the manufacturer's instructions. Membranes were blocked in Odyssey Blocking Buffer (LI-COR Biosciences) for 1 h at room temperature then incubated with antibodies against ABCA1 (Timmins, J. M. et al. Targeted inactivation of hepatic Abca1 causes profound hypoalphalipoproteinemia and kidney hypercatabolism of apoA-I. J Clin Invest 115, 1333-1342, 2005), ABCG1 (Novus Biologicals) or β-Actin (Sigma-Aldrich, St. Louis, Mo.) in the same blocking buffer at 4° C. overnight. Blots were then washed and incubated with the secondary antibody conjugated to IRDye 800CW fluorophore (LI-COR Biosciences). Proteins were detected and analyzed using the Odyssey Infrared Imaging System (LI-COR Biosciences, Lincoln, Nebr.). Band densities of ABCA1 and ABCG1 were quantified and normalized to β-actin.

Flow Cytometry

Thioglycollate elicited peritoneal macrophages of young and old mice were rinsed in FACS buffer (0.1 mM EDTA, 2% FBS, PBS Mg/Ca free), permeabilized using 0.1% Triton X 100 in 1×PBS for 15 minutes and stained for either ABCA1 or ABCG1 along with isotype controls for 1 hour. After three washes, cells were incubated with FITC-conjugated secondary antibodies. Stained cells were then analyzed using Beckman Coulter flow cytometer (Beckman Coulter, Inc., Brea, Calif.).

Oil Red O Staining

Peritoneal macrophages were stained with Oil Red O Staining Kit, according to the manufacturer's instructions (Lifeline Cell Technology, Frederick, Md.). Cells were fixed with 4% PFA for 20 min and washed twice with deionized water. Dehydrated cells with 1,2 Propanediol were incubated with pre-warmed Oil Red O solution for 30 min at 37° C. Cells were then washed with 85% 1,2 Propanediol Stain Differential solution prior to examination by microscopy.

Cholesterol Measurement

Total cholesterol content of young and old peritoneal macrophages was quantified using the Amplex Red Cholesterol Assay Kit, according to the manufacturer's instructions (Molecular Probes). In brief, 50 μl of cell lysates (diluted in reaction buffer supplied in the assay kit) were incubated with 50 μL of the Amplex Red reagent/HRP/cholesterol oxidase/cholesterol esterase solution for 30 min at 37° C. At different time points, cholesterol-associated fluorescence was measured and total cholesterol content was quantified using a cholesterol standard curve. For each sample, cellular protein content was determined and total cholesterol levels were represented as micrograms of total cholesterol per milligram of protein.

OxLDL Uptake Assay

Peritoneal macrophages isolated from young (<3 months) and old (>18 months) mice were plated on chamber slides and adherent cells were treated with 25 μg/ml DiI-oxydized LDL (oxLDL) for 24 hours (Intracel). After multiple washes, macrophages were incubated with fresh medium and DiI-oxLDL retention was examined using Zeiss LSM510 Confocal microscope.

OxLDL Efflux Assay

Young and old macrophages were preincubated for 3 hours with 25 μg/ml DiI-oxLDL following which cells were further cultured for additional 21 hours and incubated in fresh media. Extruded DiI-oxLDL in the supernatant was analyzed and fluorescence was measured using 520 nm excitation and emission detection at 564 nm.

Cholesterol Efflux Assay

Thioglycollate-elicited peritoneal macrophage from young (<3 months) and old (>18 months) mice were incubated with 5 μCi/ml [3H]cholesterol-labeled oxLDL for 24 hours. Cells were then washed and equilibrated with 2 mg/ml BSA (Sigma-Aldrich) in media for 1 hour followed by incubation for 4 hours in media containing 10 μg/ml Human ApoA1 or 50 μg/ml human HDL. Supernatants were collected and specific ApoA1/HDL-cholesterol efflux was expressed as a percentage relative to total radioactivity in cells and media.

Cholesterol Sensing Assay

Young and old macrophages were incubated with 25 μg/ml oxLDL for 24 hours following which quantitative analysis of ABCA1 and ABCG1 gene expression by real time qPCR was assessed as described above.

Vascular Endothelial Cell Proliferation Assay

Cell proliferation was measured with an adaptation of a previously described method (Khan. A. A. & Apte, R. S. An assay for macrophage-mediated regulation of endothelial cell proliferation. Immunobiology 213, 695-699, 2008). HMVECs ($1\times10^4$ cells) in log phase were cultured in 96-well round-bottomed plates for adherence. HMVECS cells were then co-cultured with peritoneal macrophages (1:25 ratio)

and incubated with 5 µCi/ml [$^3$H]thymidine (PerkinElmer) for 24 hours. Cells were harvested onto glass fiber filters (Packard) and incorporated [3H]thymidine was read using TopCount NXT (PerkinElmer).

Laser-Induced CNV in Mice

Rupture of Bruchs membrane with laser was used to initiate CNV in mice as described previously (Apte R S, Niederkorn J Y. Isolation and characterization of a unique natural killer cell inhibitory factor present in the anterior chamber of the eye. J. Immunol. 156:2667-2673, 1996). Briefly, mice were anesthetized by injecting ketamine hydrochloride (100 mg/kg) and xylazine (13.4 mg/kg) intraperitoneally, and their pupils were dilated with 1% tropicamide. Using argon green laser, four laser burns were placed around the optic nerve (0.1 second. 50 µm, and 110 mW). Seven days after laser, mice were anesthetized as described above and perfused intraventricularly with FITC-dextrin (Sigma-Aldrich). Mice were euthanized in a CO2 chamber, and their eyes were harvested for tissue processing. A dissecting microscope was used to remove the cornea and lens and to gently separate the retina from the underlying choroid and sclera.

Micro scissors were used to make four radial incisions in the sclerochoroidal "eyecup" to prepare choroidal flat mounts on glass slides. The tissues were incubated in 4% paraformaldehyde for 45 min and washed 3 times with 3% bovine serum albumin. The choroidal flat mounts were analyzed for the presence of CNV by confocal microscopy. The extent of choroidal neovascularization was quantified by Metamorph Imaging software. We used n≥5 mice for each group.

Treatment LXR Agonist

Young and old peritoneal macrophages were treated with Liver X Receptor (LXR) agonist, TO-901317 (Sigma-Aldrich, St. Louis, Mo.) for 24 hours. LXR agonist was dissolved in DMSO (vehicle) and treatment dosage ranged from 0 to 10 µM. Treated macrophages were analyzed for ABCA1 and ABCG1 gene expression and their ability to inhibit HMVECs proliferation was tested.

Old mice (>18 months) were given a daily intraperitoneal injection of vehicle, 25 mg/kg or 50 mg/kg TO-901317. After five consecutive days treatment, CNV was induced in one set of mice (5 of each group) and analyzed as described above. The second set of mice (3 of each group) was sacrificed for ABCA1 and ABCG1 gene and protein expression analysis in retina, choroid, peritoneal macrophages, brain and liver.

Oxysterol Determinations

Oxysterols were extracted from RPMI-1640 culture media of young or old peritoneal macrophages and determinations of 27-hydroxycholesterol (27-HC) and 7-ketocholesterol (7-KC) were performed as previously described (Jiang, X. et al. A sensitive and specific LC-MS/MS method for rapid diagnosis of Niemann-Pick C1 disease from human plasma. J. Lipid Res. 52, 1435-1445, 2011). 27-HC and 7-KC measurements were normalized to total proteins extracted from young or old macrophages.

MicroRNA Quantification

Total miRNA was isolated from peritoneal macrophages using mirVana kit (Ambion) and reverse transcribed with the RT$^2$ miRNA First Strand Kit (SABioscience). PCR amplifications of cDNA were performed using RT$^2$ SYBR Green qPCR (SABioscience) with specific primers for quantification of mouse miR33 and normalized to U6 as housekeeping gene.

MiR33 Transfection

Peritoneal macrophages were transfected with 50 nM miScript miR33 inhibitor (anti-miR33) or negative control inhibitor (con anti-miR) using HiPerFect Transfection reagent (Qiagen). The transfection efficiency of macrophages was assessed using BLOCK-iT Fluorescent Oligo (Invitrogen). After miR33 inhibition, target genes and proteins were analyzed by qPCR and Western blot.

DNA Methylation Analysis

DNA samples were bisultite modified using the Epitect Bisulfite kit (Qiagen) to convert unmethylated cytosines into uracils. CpG methylation was determined by Sanger sequencing the bisulfite-modified using ABI Prism Dye Terminator BigDy kit (Applied Biosystems) with the following primers: ABCA1 forward-GAAGGTTAGTAGGTTAGGGTTAGGG (SEQ ID NO:1); ABCA1 reverse-AAAAACAAAAAA-CAAAACAACTCCC (SEQ ID NO:2); ABCG1 forward-GGGTTGAGTTGGTTTAGTTTTTGTA (SEQ ID NO:3); ABCG1 reverse-ACAAACACACACCCATCTTCAAC-TAAT (SEQ ID NO:4). Sequence data was interpreted using Sequencer software (Gene Codes Corp., Ann Arbor, Mich.).

Statistics

Statistical analysis was determined by 2-tailed Student's t test and ANOVA with the use of GraphPad Prism Software. Results are presented as mean±SEM. Statistical significance was defined at P<0.05.

EXAMPLES

The present teachings including descriptions provided in the Examples that are not intended to limit the scope of any claim or aspect. Unless specifically presented in the past tense, an example can be a prophetic or an actual example. The following non-limiting examples are provided to further illustrate the present teachings. Those of skill in the art, in light of the present disclosure, will appreciate that many changes can be made in the specific embodiments that are disclosed and still obtain a like or similar result without departing from the spirit and scope of the present teachings.

Example 1

This example illustrates effects of age on cholesterol efflux.

To determine whether age altered cholesterol efflux in macrophages, we analyzed the expression patterns of ABCA1 and ABCG1 in these cells. Quantitative analysis of gene expression by real time PCR demonstrated an age-associated reduction in levels of ABCA1 and ABCG1 expression in splenic, peritoneal and eye macrophages and PBMCs (FIG. 1a-d). Analysis of ABCA1 and ABCG1 protein levels in peritoneal macrophages isolated from either young (<3 months) or old (>18 months) mice by western blotting as well as flow cytometry confirmed that reduced gene expression of ABCA1 and ABCG1 with age translated to reduced protein expression (FIG. 1e-f).

Because of the critical role of ABC transporters in lipid metabolism in macrophages, we examined whether the age-associated decrease of ABCA1 and ABCG1 altered the intracellular lipid load within macrophages and influenced formation of foam cells. Thioglycollate elicited young or old peritoneal macrophages were stained with Oil red O to visualize foam cells (FIG. 2a, arrow). Quantitative analysis of lipid-laden macrophages showed that foamy macrophages were more frequent in peritoneal macrophages collected from old mice as compared to young mice (FIG. 2b). Subsequent quantification of total cholesterol content by fluorometry confirmed the significantly increased accumulation of cholesterol in old macrophages compared to their young counterparts (21.95±0.15 vs 14.90±0.10, p<0.001) (FIG. 2c).

To test whether the senescence-associated decrease of ABC transporters affected the cholesterol efflux efficiency in macrophages, we assessed the ability of peritoneal macrophages to effectively internalize, retain and subsequently efflux lipids from oxidized low-density lipoproteins (oxLDL). Thioglycollate elicited young or old peritoneal macrophages were incubated with Dil-oxLDL for 24 hours following which cells were washed and incubated in fresh media. Intracellular accumulation of Dil-oxLDL was then examined by confocal microscopy. Macrophages from old mice had higher levels of intracellular oxLDL compared to macrophages from young mice (FIG. 2d).

Figure 8:
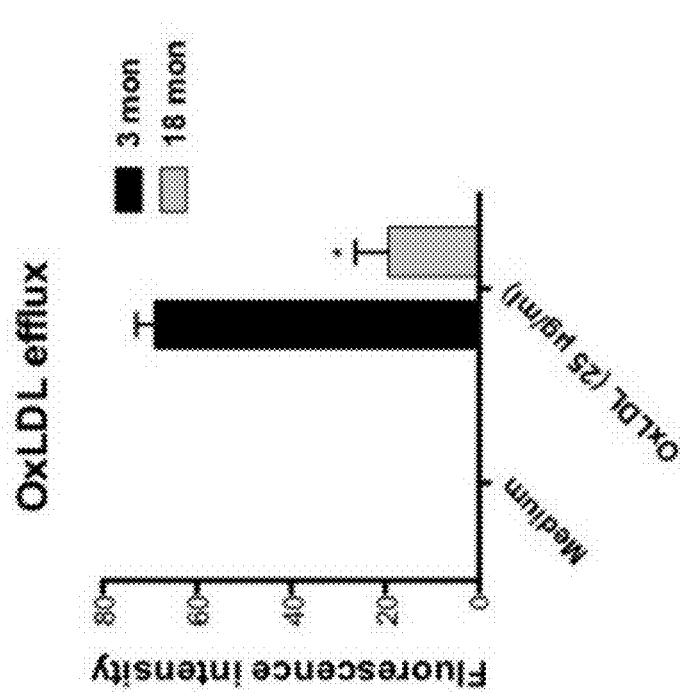
FIG. 8 illustrate age-related alteration of macrophage ability to efflux cholesterol.

In order to assess their abilities to efflux lipids, young and old macrophages were incubated with Dil-oxLDL for 3 hours following which cells were washed and incubated in fresh media for an additional 21 hours. There was no difference in the level of internalized oxLDL in young as compared to old macrophage examined by fluorescence microscopy immediately after 3 hours of incubation confirming that the influx capacity of old macrophages was not altered. However, quantitative analysis of the extruded oxLDL content showed significantly higher levels in supernatants of young macrophages compared to old cells (FIG. 8). As Dil-oxLDL is not a direct and specific measure of cholesterol efflux, we next analyzed specific cholesterol efflux of young and old macrophages, preloaded with [3H]cholesterol using ApoA1 and HDL as carriers. Macrophages were incubated with 5 µCi/ml [3H]cholesterol-labeled oxLDL for 24 hours. Cells were washed and equilibrated for 1 hour followed by incubation for 4 hours in media containing ApoA1 or HDL. Consistent with the results above, we demonstrate that cholesterol efflux is significantly reduced in old macrophages (FIG. 2e). Taken together, our findings demonstrate that reduced expression of ABC transporters in old macrophages impairs their ability to effectively efflux cholesterol.

It has been previously demonstrated that macrophages can sense alterations in extracellular cholesterol levels and effectively modulate levels of ABC transporters (Repa, J. J. et al. Regulation of absorption and ABC I-mediated efflux of cholesterol by RXR heterodimers. Science 289, 1524-1529, 2000). We next investigated the effect of cholesterol treatment on the expression patterns of ABCA1/G1 in young or old macrophages. Young macrophages demonstrated a robust increase in expression of both ABCA1 and G1 after incubation with oxLDL, while old macrophages were significantly impaired in their ability to do so (FIG. 2f-g). These findings confirm that senescent macrophages not only have reduced cholesterol efflux capacities, but also are unable to respond to exogenous lipid as efficiently as young macrophages.

Example 2

This example illustrates that Abca1 depletion affects macrophage regulation of vascular endothelial cell proliferation and pathological angiogenesis.

To determine the contribution of individual ABC transporters in age-associated dysfunction of macrophage cholesterol homeostasis, we investigated the effects of selective Abca1 or Abcg1 deletion on effector function. Recent studies have demonstrated that macrophage polarization can play a pivotal role in determining their ultimate effector functions including their ability to regulate angiogenesis (Macrophages Inhibit Neovascularization in a Murine Model of Age-Related Macular Degeneration. PLoS Med 3(8): e310, doi:10.1371/journal.pmed.0030310 2006; Kelly, J., et al., Senescence regulates macrophage activation and angiogenic fate at sites of tissue injury in mice. J. Clin. Invest. 117, 3421-3426, 2007; Mosser, D. M. The many faces of macrophage activation. J. Leukoc. Biol. 73, 209-212, 2003; Mantovani, A., et al., Macrophage polarization comes of age. Immunity 23, 344-346, 2005). To determine whether Abca1 or Abcg1 deletion affected macrophage polarization, we analyzed the cytokine gene expression patterns of peritoneal macrophages isolated from young wt, Abca1$^{-/-}$ or Abcg1$^{-/-}$ mice by quantitative real time PCR. Loss of Abca1 was associated with a significant decrease in IL-6 and FasL expression and an upregulation of IL-10 expression, consistent with an alternatively activated phenotype (FIG. 3a). Expression levels of TNF-α and IL-12 were not altered. As previously shown, this cytokine signature is characteristic of pro-angiogenic macrophages (Macrophages Inhibit Neovascularization in a Murine Model of Age-Related Macular Degeneration. PLoS Med 3(8): e310, doi:10.1371/journal.pmed.0030310 2006; Mosser, D. M. The many faces of macrophage activation. J. Leukoc. Biol. 73, 209-212, 2003; Mantovani, A., et al., Macrophage polarization comes of age. Immunity 23, 344-346, 2005). In contrast, loss of Abcg1 had no effect on global macrophage polarization to either classical or alternatively activated cells as both IL-6 and IL-10 gene expression were reduced significantly without any associated change in FasL expression (FIG. 9a).

FIG. 9 illustrates that the deletion of Abcg1 has no effect on macrophage-mediated regulation of vascular proliferation. (a) Quantitative mRNA analysis of IL-6, FasL and IL-10 in wt (Abcg1+/+) and ABCG1-deficient (Abcg1−/−) macrophages. (b) Assessment of the ability of Abcg1+/+ or Abcg1−/− macrophages to inhibit proliferation of HMVECs. Laser-induced CNV in Abcg1+/+ or Abcg1−/− mice was examined by confocal microscopy (c) and CNV (white circle) volume quantified (d). Statistically significant difference P<0.01, *P<0.001.

Next, we investigated the ability of Abca1$^{-/-}$ and Abcg1$^{-/-}$ macrophages to inhibit vascular endothelial cell proliferation in vitro using HMVECs and to regulate pathologic angiogenesis in vivo using the injury-induced CNV assay as described previously and in Methods (Kelly, J., et al., Senescence regulates macrophage activation and angiogenic fate at sites of tissue injury in mice. J. Clin. Invest. 117, 3421-3426, 2007). In co-cultures, Abca1$^{-/-}$ macrophages from young mice lost their ability to inhibit HMVECs proliferation as compared to macrophages from age-matched wt mice or from Abcg1−/− young macrophages (FIG. 3b and FIG. 9b). These results combined with previous findings that old macrophages lose the ability to regulate vascular proliferation and CNV suggest that Abca1$^{-/-}$ macrophages demonstrate an accelerated senescence program. We investigated this in vivo in the injury-induced CNV model. As anticipated, CNV volumes were significantly higher in mice whose macrophages were deficient in Abca1 as compared to wild type littermates (FIG. 3c-d). In contrast, CNV volumes in Abcg1$^{-/-}$ mice were comparable to littermate controls confirming an ability of these cells to inhibit CNV (FIG. 9c-d). These results demonstrate that ABCA1 is the primary regulator of macrophage polarization and that 'young' macrophages lacking Abca1 have the same cytokine polarization and functional deficits i.e. pro-angiogenic behavior as 'old' wild type macrophages.

Example 3

This example illustrates that a cholesterol-rich diet accelerates a senescent macrophage phenotype.

As shown in FIG. 2, ABCA1/G1 transporters within macrophages regulate intracellular cholesterol efflux. We next investigated the effect of chronic dietary lipid/cholesterol burden on macrophage function using diet-induced obesity (DIO) mice as a model of high fat/cholesterol fed mice. Quantitative analysis of intracellular cholesterol content demonstrated that DIO macrophages had significantly higher levels of total cholesterol compared to age-matched controls at both 3 and 6 months of age (FIG. 3e). To determine whether high fat/cholesterol stress altered the ability of DIO macrophages to regulate vascular proliferation, we incubated young DIO macrophages with HMVECs and assessed their proliferation. DIO macrophages were unable to inhibit HMVECs proliferation (FIG. 3f). In addition, DIO macrophages demonstrated an impaired ability to regulate CNV in vive (FIG. 3g-h) indicating that chronic fat/cholesterol stress can impair the ability of macrophages from young mice to regulate pathological vascular proliferation and angiogenesis. These data also suggest that higher dietary lipid can potentially accelerate the programmatic changes associated with senescence within macrophages.

Example 4

This example illustrates that LXR agonists restore in senescent macrophages their functional capacity to regulate pathological angiogenesis.

Our data show that age-associated reduction in expression of ABC transporters impairs the efflux capacity of macrophages and results in increased cholesterol accumulation. Loss of Abca1 also translated into a loss of the ability of these cells to regulate angiogenesis. We therefore investigated whether restoring the efflux capacity of macrophages in old mice could improve their effector functions. Recent studies have shown that transcriptional nuclear receptors such as Liver X Receptors (LXRs) were direct enhancers of ABC transporters expression in macrophages (Repa, J. J., et al., Regulation of absorption and ABC I-mediated efflux of cholesterol by RXR heterodimers. Science 289, 1524-1529, 2000).

Treatment of peritoneal young or old macrophages with LXRs synthetic agonist (TO-901317, Cayman Chemical Company, Ann Arbor, Mich.) induced a dose-dependent upregulation of both ABCA1 and ABCG1 gene expression (FIG. 4a-b). Importantly, this ligand-dependent increase of ABC transporters was higher in old macrophages suggesting retained responsiveness of old macrophages to LXR agonists despite low baseline levels of ABCA1/G1 expression (as shown in FIG. 1a-d) allowing old cells to reach the expression levels of ABCA1 and ABCG1 comparable to that seen in young macrophages. Although the ability of old macrophages to upregulate ABCA1/G1 transporter expression in response to exogenous cholesterol (oxLDL) was dampened as seen in FIG. 2f-g, they were able to respond robustly to direct LXR stimulation by synthetic ligand (TO-901317).

It has been previously demonstrated that LXR can be regulated by endogenously-synthesized cholesterol oxidation products (oxysterols) such as 27-hydroxycholesterol (27-HC) or non-oxysterol mediators (TO-901317) (Repa, J. J., et al., Regulation of absorption and ABC1-mediated efflux of cholesterol by RXR heterodimers. Science 289, 1524-1529, 2000; Janowski, B. A., et al., An oxysterol signalling pathway mediated by the nuclear receptor LXR alpha. Nature 383, 728-731, 1996; Repa, J. J. & Mangelsdorf, 1). J. Nuclear receptor regulation of cholesterol and bile acid metabolism. Curr. Opin. Biotechnol. 10, 557-563, 1999).

An analysis of baseline cell-associated oxysterol content of young and old macrophages at baseline showed a 2-fold increase in 27-HC in old macrophages (FIG. 4c). The increase in 27-HC was accompanied by a commensurate 2-fold increase in 7-ketocholesterol (7-KC). While 27-HC is an activator of the LXR pathway (Fu, X. et al. 27-hydroxycholesterol is an endogenous ligand for liver X receptor in cholesterol-loaded cells. J. Biol. Chem. 276, 38378-38387, 2001), numerous studies have shown that 7-KC can effectively interfere with LXR activation and cholesterol efflux (Gelissen, I. C. et al. Sterol efflux is impaired from macrophage foam cells selectively enriched with 7-ketocholesterol. J. Biol. Chem. 271, 17852-17860, 1996; Gelissen, I. C., et al., Oxysterol efflux from macrophage foam cells: the essential role of acceptor phospholipid. J. Lipid Res. 40, 1636-1646, 1999; Kritharides, L., et al., Apolipoprotein A-I-mediated efflux of sterols from oxidized LDL-loaded macrophages. Arterioscler. Thromb. Vasc. Biol. 15, 276-289, 1995). As seen in FIG. 4c, the absolute increase in 7-KC levels was 17-fold greater than that of 27-HC, offering a possible explanation as to why old macrophages are unable to respond as efficiently to exogenous cholesterol stimulation but respond robustly to synthetic agonists. These data suggest the possibility of reversing some of the programmatic dysfunctionality seen in these cells with age.

In order to confirm this hypothesis, we co-cultured LXR agonist (TO-901317)-treated young or old macrophages with HMVECs and analyzed their ability to inhibit endothelial cell proliferation. As shown in FIG. 4d, LXR agonist treatment of old macrophages completely restored their ability to inhibit endothelial cell proliferation. Treatment of Abca1$^{-/-}$ macrophage with LXR agonist does not restore their ability to inhibit HMVECs proliferation. These results confirm that downregulation of ABCA1 (not ABCG1) is the basis of the impaired function observed in old macrophages.

Old mice were then treated with intraperitoneal injections of vehicle (DMSO) or TO-901317 at 25 or 50 mg/kg/day for 5 days prior laser induction of CNV. Quantitative analysis of gene expression showed that treated mice at both doses had strong systemic upregulation of ABCA1 and ABCG1 expression compared to vehicle treated mice (FIG. 4e-g and FIG. 10).

Figure 10A:
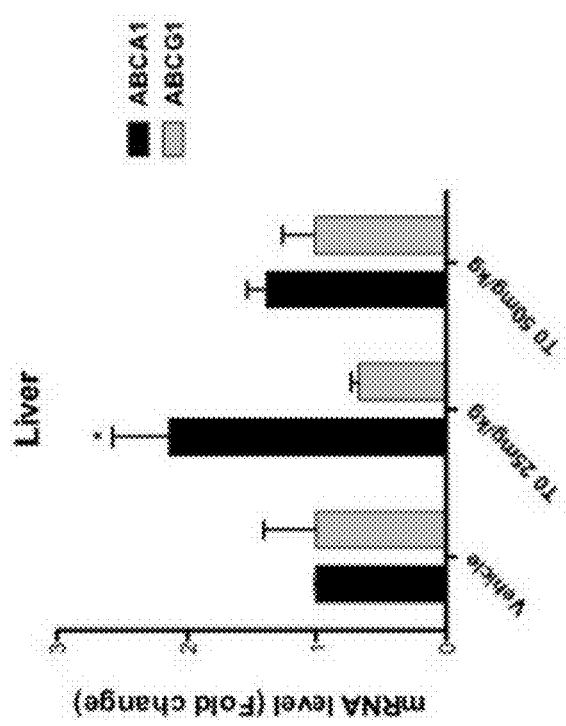
FIG. 10A-B illustrate the effects of LXR agonist treatment on ABC transporter expression.
Figure 10B:
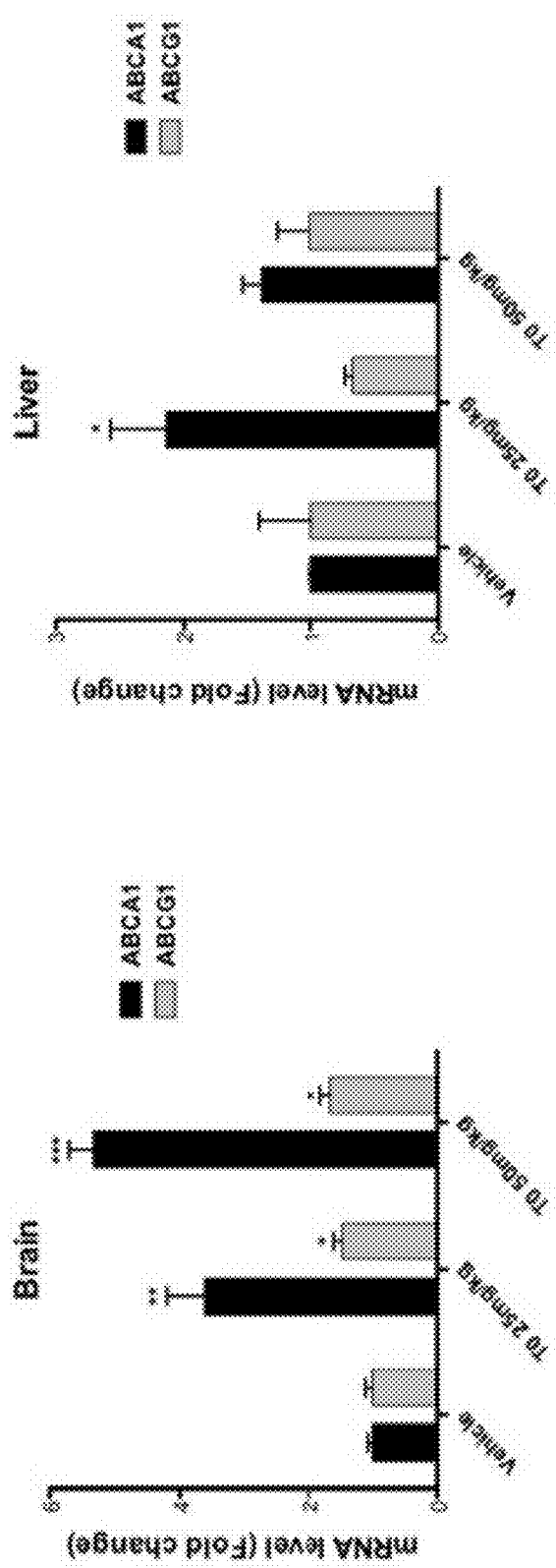

FIG. 10 illustrates the effects of LXR agonist treatment on ABC transporter expression. Quantitative analysis of mRNA levels of ABCA1 and ABCG1 in brain (a) and liver (b) of old mice, treated for 5 days with vehicle, 25 mg/kg or 50 mg/kg of TO-901317. Statistically significant difference *P<0.05, P<0.01, *P<0.001, compared to vehicle treatment.

Figure 4H:
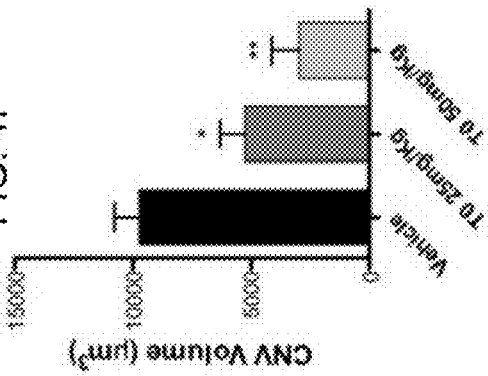
Figure 4I:
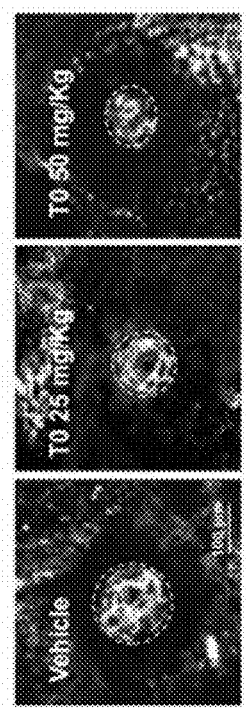

In addition. LXR-agonist treatment of old mice resulted in a significant and dose dependent reduction in CNV compared to vehicle treated old mice thus restoring their functional capacity to regulate pathological vascular proliferation (FIG. 4h-i). Taken together, these results conclusively demonstrate that LXR agonists restore in old macrophages effector capabilities that are similar to those observed in young macrophages.

Example 5

This example illustrates age-related reduction of ABCA1 expression in human PBMCs.

The above data demonstrate that senescent macrophages have impaired cholesterol efflux capacities that lead to a loss of their ability to regulate vascular proliferation. This impairment in macrophage function is associated with a loss of ABCA1. We next investigated the expression levels of ABCA1/G1 in PBMCs isolated from young (age range 25-34 years, n=9) and old (age range 67-87 years, n=9) donors. In these experiments, total protein extracts were analyzed for ABCA1/G1 expression and representative immunoblots are shown in FIG. 5a. Densitometric analysis normalized to β-actin expression showed that ABCA1 expression level was significantly reduced in old compared to young donors while ABCG1 protein expression was unchanged (FIG. 5b-c).

Figure 11C:
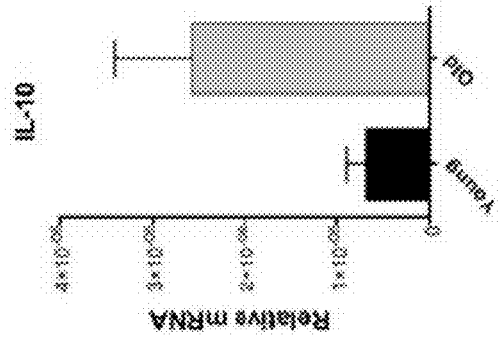
FIG. 11A-C illustrate IL-10, ABCA1 and ABCG1 gene expression in human PBMCs of young and old donors.
Figure 11B:
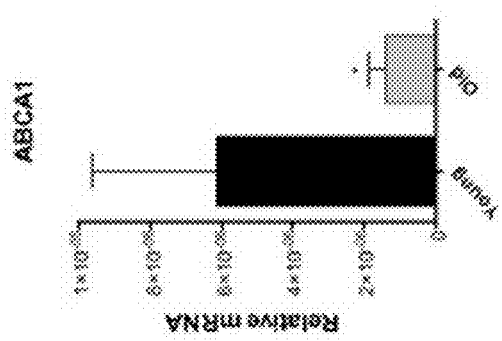
Figure 11A:
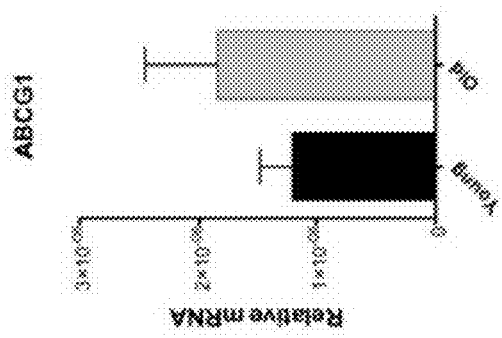

These findings are consistent with quantitative gene expression analysis demonstrating that ABCA1 gene expression was 2.5 fold lower in old donors while ABCG1 expression was not significantly different (FIG. 11b-c). In addition, PBMCs from old donors had higher levels of IL-10 expression compared to young, confirming their phenotype as alternatively activated cells (FIG. 11a). Immunohistochemistry of a CNV membrane isolated from a patient during sub-retinal surgery confirmed the presence of CD68 positive macrophages that have reduced ABCA1 expression when compared to other cell types within the lesion (FIG. 5d, arrows).

Example 6

This example illustrates age-related overexpression of Mir33 repressed macrophage regulation of vascular proliferation.

Figure 6A:
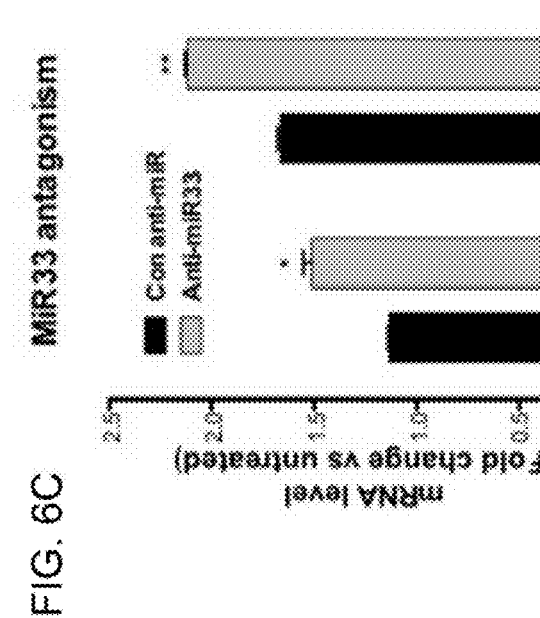
FIG. 6A-E illustrate MiR33 modulates macrophage regulation of vascular proliferation.

We have shown that aging altered macrophage expression of ABCA1 and ABCG1 that resulted in defective cholesterol efflux and subsequent impairment in their capacity to regulate pathological angiogenesis. We next investigated the mechanisms that led to the age-associated decline in the expression of ABC transporters. To determine whether epigenetic mechanisms were involved in this process, the methylation pattern of Abca1 and Abcg1 promoters by bisulfite modified CpG Sanger sequencing. There was no significant difference in the frequency or pattern of methylation of the promoter regions of these genes between young and old macrophages (FIG. 12). Recent studies have shown that a highly conserved microRNA, miR33 regulates the expression of genes involved in cellular cholesterol metabolism, among them ABCA1 and ABCG1 (Najafi-Shoushtari, S. H. et al. MicroRNA-33 and the SREBP host genes cooperate to control cholesterol homeostasis. Science 328, 1566-1569, 2010; Rayner, K. J. et al. MiR-33 contributes to the regulation of cholesterol homeostasis. Science 328, 1570-1573, 2010; Marquart, T. J., et al., miR-33 links SREBP-2 induction to repression of sterol transporters. Proc. Natl. Acad. Sci. USA 107, 12228-12232, 2010; Rayner, K. J. et al. Antagonism of miR-33 in mice promotes reverse cholesterol transport and regression of atherosclerosis. J. Clin. Invest. 121, 2921-2931, 2011). We next examined miR33 expression in young and old macrophages. As shown in FIG. 6a, miR33 expression was significantly higher in old macrophages as compared to young, consistent with reduced expression of ABCA1 and ABCG1 observed in aged macrophages.

Figure 6B:
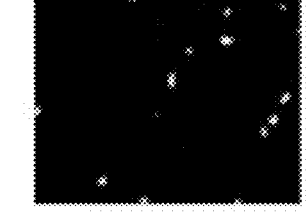
Figure 6C:
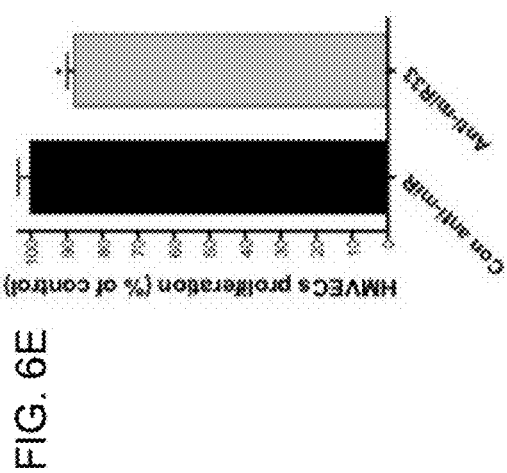
Figure 6D:
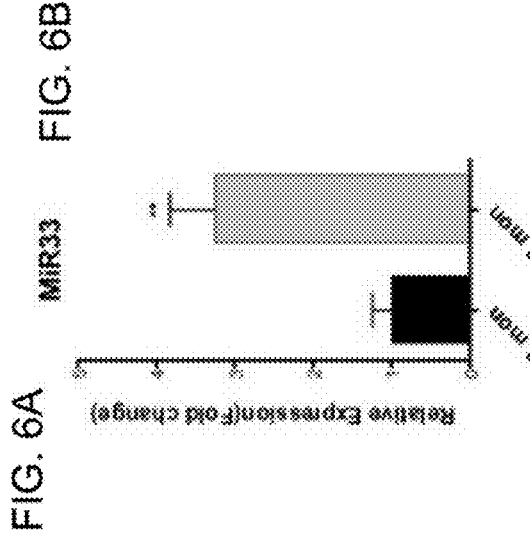
Figure 6E:
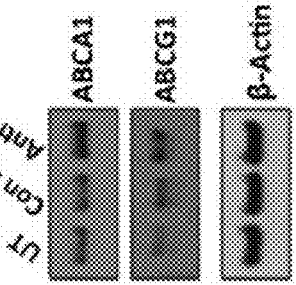
Figure 7A:
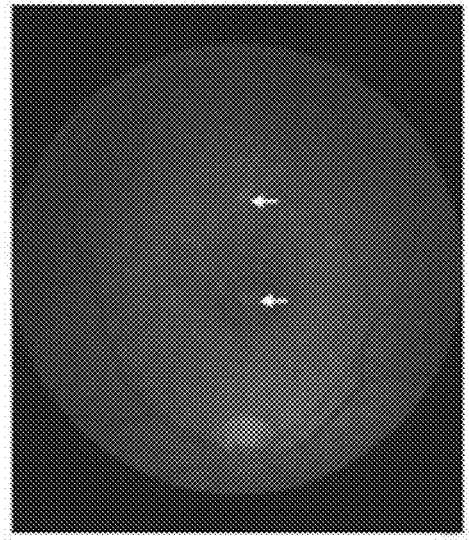
FIG. 7A-B illustrate biomicroscopic findings in AMD. Clinical photograph of the retina of a patient with wet AMD (a) illustrates the development of CNV characterized by subretinal blood (arrow). An eye with dry AMD (b) demonstrates the presence of lipid rich drusen (arrow).
Figure 7B:

Based on these findings, we hypothesized that antagonism of miR33 in macrophages might enhance their regulation of vascular proliferation. Macrophages were transfected with miR33 inhibitor (anti-miR33) or negative control inhibitor (con anti-miR) and expression of ABC transporters expression was assessed. Efficacy of microRNA transfection was confirmed using fluorescent RNA oligomer as shown in FIG. 6b. Inhibition of miR33 resulted in a significant increase in mRNA and protein levels of both ABCA1 and ABCG1 (FIG. 6c-d). In addition, antagonism of endogenous miR33 improved the ability of macrophages to inhibit vascular endothelial cell proliferation (FIG. 6e).

References cited herein are incorporated by reference, each in its entirety.

What is claimed is:

1. A method of treating an ocular disease characterized by choroidal neovascularization (CNV) in a subject in need thereof, comprising administering to the subject a therapeutically effective amount of an inhibitor of cholesteryl ester transfer protein (CETP) activity.

2. A method in accordance with claim 1, wherein the inhibitor of CETP activity is selected from the group consisting of ethyl (2R,4S)-4-({[3,5-bis(trifluoromethyl)phenyl]methyl}(methoxycarbonyl)amino)-2-ethyl-6-(trifluoromethyl)-1,2,3,4-tetrahydroquinoline-1-carboxylate (Torcetrapib), (4S,5R)-5-[3,5-bis(trifluoromethyl)phenyl]-3-({2-[4-fluoro-2-methoxy-5-(propan-2-yl)phenyl]-5-(trifluoromethyl)phenyl}methyl)-4-methyl-1,3-oxazolidin-2-one (Anacetrapib) and S-[2-({[1-(2-ethylbutyl)cyclohexyl]carbonyl}amino)phenyl]2-methylpropanethioate (Dalcetrapib).

3. A method in accordance with claim 1, wherein the administering a therapeutically effective amount of an inhibitor of CETP activity comprises intraocularly injecting a pharmaceutically acceptable formulation comprising the inhibitor.

4. A method in accordance with claim 1, wherein the administering a therapeutically effective amount of an inhibitor of CETP activity comprises administering to an eye of the subject a pharmaceutically acceptable eye drop formulation comprising the inhibitor.

5. A method in accordance with claim 1, wherein the administering a therapeutically effective amount of inhibitor of CETP activity comprises administering the inhibitor orally in a pharmaceutically acceptable formulation.

6. A method in accordance with claim 1, wherein the administering a therapeutically effective amount of inhibitor of CETP activity comprises administering the inhibitor parenterally in a pharmaceutically acceptable formulation.

* * * * *

SEQUENCE LISTING

```
<160> NUMBER OF SEQ ID NOS: 6

<210> SEQ ID NO 1
<211> LENGTH: 25
<212> TYPE: DNA
<213> ORGANISM: Homo sapiens

<400> SEQUENCE: 1
gaaggttagt aggttagggt taggg                                          25

<210> SEQ ID NO 2
<211> LENGTH: 25
<212> TYPE: DNA
<213> ORGANISM: Homo sapiens

<400> SEQUENCE: 2
aaaaacaaaa aacaaaacaa ctccc                                          25

<210> SEQ ID NO 3
<211> LENGTH: 25
<212> TYPE: DNA
<213> ORGANISM: Homo sapiens

<400> SEQUENCE: 3
gggttgagtt ggtttagttt ttgta                                          25

<210> SEQ ID NO 4
<211> LENGTH: 25
<212> TYPE: DNA
<213> ORGANISM: Homo sapiens

<400> SEQUENCE: 4
acaaacacac ccatcttcaa ctaat                                          25
```

```
<210> SEQ ID NO 5
<211> LENGTH: 73
<212> TYPE: DNA
<213> ORGANISM: Homo sapiens

<400> SEQUENCE: 5
agtcgaattt ataaaaggaa ttagtcgcgg taaaaattag taatttcgag ggcgagcgag      60
cgggtcggga tcg                                                        73

<210> SEQ ID NO 6
<211> LENGTH: 62
<212> TYPE: DNA
<213> ORGANISM: Homo sapiens

<400> SEQUENCE: 6
gtgggtaggg gcggggtcgg ggcgtagtcg gaattcgcgt agagcgtcgc ggaggagtag      60
ga                                                                    62
```